US012735464B2

(12) United States Patent
Saarma et al.

(10) Patent No.: US 12,735,464 B2
(45) Date of Patent: Sep. 15, 2026

(54) C-TERMINAL CDNF AND MANF FRAGMENTS, PHARMACEUTICAL COMPOSITIONS COMPRISING SAME AND USES THEREOF

(71) Applicant: MyNeuroCure Oy, Helsinki (FI)

(72) Inventors: Mart Saarma, Helsinki (FI); Mikko Airavaara, Helsinki (FI); Merja Voutilainen, Helsinki (FI); Li Ying Yu, Helsinki (FI); Maria Lindahl, Helsinki (FI)

(73) Assignee: MyNeuro Cure Oy, Helsinki (FI)

( * ) Notice: Subject to any disclaimer, the term of this patent is extended or adjusted under 35 U.S.C. 154(b) by 0 days.

(21) Appl. No.: 16/610,532

(22) PCT Filed: May 4, 2018

(86) PCT No.: PCT/FI2018/050332

§ 371 (c)(1),
(2) Date: Nov. 4, 2019

(87) PCT Pub. No.: WO2018/202957

PCT Pub. Date: Nov. 8, 2018

(65) Prior Publication Data

US 2020/0071372 A1 Mar. 5, 2020

(30) Foreign Application Priority Data

May 4, 2017 (FI) ..................................... 20175392

(51) Int. Cl.
*C07K 14/475* (2006.01)
*A61K 38/00* (2006.01)
*A61P 25/28* (2006.01)

(52) U.S. Cl.
CPC ............ *C07K 14/475* (2013.01); *A61P 25/28* (2018.01); *A61K 38/00* (2013.01)

(58) Field of Classification Search
None
See application file for complete search history.

(56) References Cited

U.S. PATENT DOCUMENTS 3,773,919 A 11/1973 Boswell et al.

FOREIGN PATENT DOCUMENTS

| | | | |
|---|---|---|---|
| EP | 58481 | B2 | 5/2003 |
| EP | 1969003 | B1 | 9/2010 |
| WO | WO02074956 | A2 | 9/2002 |
| WO | WO 02/079246 | * | 10/2002 |
| WO | WO02079246 | A2 | 10/2002 |
| WO | WO2007068803 | A1 | 6/2007 |
| WO | WO2009133247 | A1 | 11/2009 |
| WO | WO2013034805 | A1 | 3/2013 |
| WO | WO2014191630 | A2 | 12/2014 |
| WO | WO2015149005 | A1 | 10/2015 |
| WO | WO2015200469 | A1 | 12/2015 |
| WO | WO2016057579 | A1 | 4/2016 |
| WO | WO2018202957 | A1 | 11/2018 |

OTHER PUBLICATIONS

Aalto et al: Large-scale production of dsRNA and siRNA pools for RNA interference utilizing bacteriophage phi6 RNA-dependent RNA polymerase. RNA. 2007, vol. 13, pp. 422-429.
Airavaara et al: CDNF protects the nigrostriatal dopamine system and promotes recovery after MPTP treatment in mice. Cell Transplant, 2012, vol. 21(6), pp. 1213-1223.
Airavaara et al: Mesencephalic astrocyte-derived neurotrophic factor reduces ischemic brain injury and promotes behavioral recovery in rats. J.Comp. Neurol., 2009, vol. 515 (1), pp. 116-124.
Bai et al: Conserved roles of C. elegans and human MANFs in sulfatide binding and cytoprotection. Nat Commun, 2018-03-01, vol. 9(1), p. 897.
Bode et al: Constrained cell penetrating peptides. Drug Discovery Today: Technologies, 2017, vol. 26, pp. 33-42.
Borrelli et al: Cell Penetrating Peptides as Molecular Carriers for Anti-Cancer Agents. Molecules, Jan. 31, 2018, vol. 23(2).
Chen et al: A model of focal ischemic stroke in the rat: reproducible extensive cortical infarction. Stroke, 1986, vol. 17(4), pp. 738-743.
Dornburg: Reticuloendotheliosis viruses and derived vectors. Gene Therap., 1995, vol. 2, pp. 301-310.
Gurney et al: Benefit of vitamin E, riluzole, and gabapentin in a transgenic model of familial amyotrophicl ateral sclerosis. Ann Neurol, 1996, vol. 39 (2), pp. 147-157.
Hamner et al: Functional characterization of two splice variants of rat bad and their interaction with Bcl-w in sympathetic neurons. Mol. Cell. Neurosci., 2001, vol. 17, pp. 97-106.
Hellman et al: Mesencephalic astrocyte-derived neurotrophic factor (MANF) has a unique mechanism to rescue apoptotic neurons. Journal of Biological Chemistry, Jan. 2011, vol. 286, No. 4, pp. 2675-2680.
Kalafatovic et al: Cell-Penetrating Peptides: Design Strategies beyond Primary Structure and Amphipathicity. Molecules, Nov. 8, 2017, vol. 22(11).

(Continued)

*Primary Examiner* — Sergio Coffa
(74) *Attorney, Agent, or Firm* — Laine IP Oy

(57) ABSTRACT

The present invention provides a C-terminal CDNF fragment sequence or a sequence which has at least 90% homology to said sequence. The C-terminal CDNF fragment protects ER stressed neurons, motoneurons and dopaminergic neurons and the fragment is capable of penetrating neuronal cell membrane as well as the blood-brain-barrier. The present invention further provides said fragment and pharmaceutical compositions comprising said fragment for use in treatments of degenerative diseases and disorders including central nervous system diseases, diabetes and retinal disorders. The present invention is also providing a C-terminal MANF fragment sequence or a sequence which has at least 90% homology to the said sequence and pharmaceutical compositions comprising said MANF fragment for use in the treatment of degenerative diseases and disorders including central nervous system diseases, diabetes and retinal disorders.

13 Claims, 16 Drawing Sheets

Specification includes a Sequence Listing.

(56) References Cited

OTHER PUBLICATIONS

Kristensen et al: Applications and Challenges for Use of Cell-Penetrating Peptides as Delivery Vectors for Peptide and Protein Cargos. Int. J. Mol. Sci., 2016, vol. 17, p. 185.
Lindahl et al: MANF is indispensable for the proliferation and survival of pancreatic β-cells. Cell Reports, 2014, vol. 7(2), pp. 366-375.
Lindholm et al: Neuronal apoptosis inhibitory protein: Structural requirements for hippocalcin binding and effects on survival of NGF-dependent sympathetic neurons. Biochim. Biophys Acta., vol. 1600, pp. 138-147.
Lindholm et al: Novel CDNF/MANF family of neurotrophic factors. Dev. Neurobiol., 2010, vol. 70, pp. 360-371.
Lindholm et al: Novel neurotrophic factor CDNF protects and rescues midbrain dopamine neurons in vivo. Nature, 2007, vol. 448, pp. 73-77.
Lindström et al: Characterization of the Structural and Functional Determinants of MANF/CDNF in *Drosophila* In Vivo Model. PLOS ONE, 2013, vol. 8(9).
Liu et al: Key subdomains in the C-terminal of cerebral dopamine neurotrophic factor regulate the protein secretion. Biochemical and Biophysical Research Communications, Sep. 2015, vol. 465, No. 3, pp. 427-432.
Marino et al: Overall, Protein Termini and Their Modifications Revealed by Positional Proteomics. ACS Chem. Biol., 2015, vol. 10, pp. 1754-1764.
Nadella et al: Transient transfection of human CDNF gene reduces the 6-hydroxydopamine-induced neuroinflammation in the rat substantia nigra. J. Neuroinflammation, 2014, vol. 11, p. 209.
Neves et al: Immune modulation by MANF promotes tissue repair and regenerative success in the retina. Science, Jul. 1, 2016, vol. 353(6294).
Oakes et al: The Role of Endoplasmic Reticulum Stress in Human Pathology. Rev. Pathol. Mech. Dis., 2015, vol. 10, pp. 173-194.
Parkash et al: The structure of the conserved neurotrophic factors MANF and CDNF explains why they are bifunctional. Protein Eng. Des. Sel., 2009, vol. 22, pp. 233-241.
Penttinen et al: Characterization of a new low-dose 6-hydroxydopamine model of Parkinson's disease in rat. J Neurosci Res. Jan. 13, 2016.
Shibata: Transgenic mouse model for familial amyotrophic lateral sclerosis with superoxide dismutase-1 mutation. Neuropathology, 2001, vol. 21(1), pp. 82-92.
Sun et al: Mutational analysis of N-Bak reveals different structural requirements for antiapoptotic activity in neurons and proapoptotic activity in nonneuronal cells. Mol. Cell. Neurosci., 2003, vol. 23, pp. 134-143.
Sun et al: Neuron-specific Bcl-2 homology 3 domain-only splice variant of Bak is anti-apoptotic in neurons, but pro-apoptotic in non-neuronal cells. J. Biol. Chem, 2001, vol. 276, pp. 16240-16247.
Voutilainen et al: Chronic infusion of CDNF prevents 6-OHDA-induced deficits in a rat model of Parkinson's disease. Exp. Neurol., 2011, vol. 228, pp. 99-108.
Voutilainen et al: Evidence for an Additive Neurorestorative Effect of Simultaneously Administered CDNF and GDNF in Hemiparkinsonian Rats: Implications for Different Mechanism of Action. ENEURO, Mar. 13, 2017, vol. 4(1).
Yu et al: Death receptors and caspases but not mitochondria are activated in the GDNF- or BDNF-deprived dopaminergic neurons. J. Neurosci., 2008, vol. 28, pp. 7467-7475.
Yu et al: GDNF-deprived sympathetic neurons die via a novel nonmitochondrial pathway. J.Cell Biol., 2003, vol. 163, pp. 987-997.
Yu et al: Survival assay of transiently transfected dopaminergic neurons. J. Neurosci. Methods, 2008, vol. 169, pp. 8-15.
Zhao et al: Mesencephalic astrocytederived neurotrophic factor inhibits oxygen-glucose deprivation-induced cell damage and inflammation by suppressing endoplasmic reticulum stress in rat primary astrocytes. J. Mol. Neurosci, 2013, vol. 51(3), pp. 671-678.
Lindahl et al: Unconventional neurotrophic factors CDNF and MANF: Structure, physiological functions and therapeutic potential. Neurobiology of Disease, vol. 97, Jul. 9, 2016.
Voutilainen et al: Mesencephalic Astrocyte-Derived Neurotrophic Factor Is Neurorestorative in Rat Model of Parkinson's Disease. Journal of Neuroscience, Jul. 29, 2009, vol. 29, No. 30, pp. 9651-9659.
Voutilainen et al: Therapeutic potential of the endoplasmic reticulum located and secreted CDNF/MANF family of neurotrophic factors in Parkinson's disease. FEBS Letters, Oct. 9, 2015, Amsterdam, vol. 589, No. 24, pp. 3739-3748.

* cited by examiner

Signal sequence

ER retention 6 9 40 51 82 93 127 130

H.s.MANF

21

RTDL

158

11 14 45 56 87 98 132 135

H.s.CDNF

26

KTEL

161

| | CDNF | C-CDNF | PCR3.1 | uninjected,TM 2uM | uninjected, NGF+ |
|---|---|---|---|---|---|
| 72hr | 59.05 | 55.90 | 34.53 | 30.15 | 100 |

| | CDNF | C-CDNF |
|---|---|---|
| Ratio | 1.96 | 1.85 |

| | CDNF(TM+) | C-CDNF(TM+) | PBS (TM+) | uninjected, TM+ | NGF+ |
|---|---|---|---|---|---|
| 72hr | 68.41 | 71.00 | 32.34 | 29.02 | 100 |

| | CDNF(TM+) | C-CDNF(TM+) |
|---|---|---|
| Ratio to PBS | 2.11 | 2.20 |

| | C-MANF 500 | no factor |
|---|---|---|
| % GDNF | 86.24 | 72.80 |

| | C-MANF 500 |
|---|---|
| Ratio | 1.18 |

| | C-CDNF 10 | C-CDNF 100 | C-CDNF 500 | no factor |
|---|---|---|---|---|
| % GDNF | 77.95 | 88.97 | 86.27 | 71.62 |

| | C-CDNF 10 | C-CDNF 100 | C-CDNF 500 |
|---|---|---|---|
| Ratios | 1.09 | 1.24 | 1.20 |

hCDNF C61 = SEQ ID NO:4
hMANF C63 = SEQ ID NO:5

C-TERMINAL CDNF AND MANF FRAGMENTS, PHARMACEUTICAL COMPOSITIONS COMPRISING SAME AND USES THEREOF

SEQUENCE LISTING STATEMENT

A Sequence Listing in ST.26 XML format is submitted herewith as a separate electronic file entitled HY18US_Sequence_Listing_ST26.xml, created on Apr. 9, 2026, and having a file size of 14,683 bytes. The Sequence Listing is incorporated by reference in its entirety into the specification of this application.

FIELD OF THE INVENTION

The present invention relates to the fields of bioactive protein fragments and cell membrane-penetrating peptides and also to the field of neurotrophic factors and endoplasmic reticulum (ER) located proteins, and more particularly to the field of treating degenerative diseases or disorders such as central nervous system diseases, diabetes and retinal disorders.

BACKGROUND OF THE INVENTION

Neurotrophic factors cerebral dopamine neurotrophic factor (CDNF) and mesencephalic astrocyte-derived neurotrophic factor (MANF) (Lindholm and Saarma, 2010; Lindahl et al., 2017) are currently the most efficient proteins for the treatment of rats in the 6-OHDA model of Parkinson's disease (PD). Both factors potently prevent the 6-OHDA-induced behavioral and histological symptoms of Parkinson's disease when applied before the toxin (Lindholm et al., 2007; Voutilainen et al., 2009). More importantly, post-treatment (i.e. treatment after 6-OHDA induction) with either factor efficiently restored the normal motor behavior and dopaminergic innervations of the striatum when applied at the stage when the 6-OHDA-induced symptoms of the Parkinson's disease are already far-reaching (Lindholm et al., 2007; Voutilainen et al., 2011). CDNF protects and repairs dopamine neurons also in mouse and rhesus monkey MPTP models of Parkinson's disease. In the monkey MPTP model, as well as in the severe rodent 6-OHDA model it is more efficient than glial cell line-derived neurotrophic factor (GDNF) in restoring dopamine neurons in substantia nigra pars compacta (SNPc) and restoring motor behavior (Voutilainen et al., 2011; Airavaara et al., 2012: Voutilainen et al., 2015). The mechanisms behind the neuronal protection for these factors are not fully clear but it has been suggested that in addition to the activation of classical survival promoting anti-apoptotic pathways, they regulate unfolded protein response (UPR) pathways, which aim at alleviating oxidative- and ER stress depressing ER-stress-induced apoptotic cell death (Lindahl et al., 2014; Lindahl et al., 2017, Voutilainen et al., 2017). Many pathophysiological conditions and degenerative diseases including diabetes mellitus and neurodegenerative diseases such as Parkinson's disease, Alzheimer's disease (AD), amyotrophic lateral sclerosis (ALS) and Huntington's disease (HD) are associated with protein misfolding and aggregation that triggers ER stress and activation of the UPR pathways. Accordingly, the effect of CDNF and MANF has been shown in various central nervous system diseases (WO2009133247; WO2007068803; and Airavaara et al, 2009). In addition, CDNF and MANF suppress neuroinflammation, which is involved in the pathophysiology of most if not all CNS diseases and injuries (Nadella et al, 2014; Neves et al., 2016; Zhao et al, 2013).

Further, WO2014191630 discloses a genetically-modified non-human animal comprising a disrupted allele for the gene that naturally encodes and expresses a functional MANF gene, wherein said animal displays progressive postnatal reduction of pancreatic beta cell mass due to the disrupted and non-functional MANF gene. A gene therapy vector delivering effective amount of a MANF or CDNF polypeptide or a functional fragment thereof for use in the intrapancreatic treatment of type 1 or type 2 diabetes is also suggested. Further, Lindahl et al., 2014, disclose that the MANF protein is indispensable for the proliferation and survival of pancreatic beta cells thereby constituting a therapeutic candidate for beta cell protection and regeneration.

WO2013034805 discloses cell-penetrating MANF or CDNF peptides with the length of 4-40 amino acids comprising the sequence CXXC for use in the treatment of Alzheimer's disease, Parkinson's disease, amyotrophic lateral sclerosis, stroke, peripheral neuropathy, epilepsy, diabetes or drug addiction.

Structural studies of CDNF and MANF have shown that these proteins consist of two domains: a saposin-like N-terminal domain (Parkash et al., 2009) and a SAP-like C-terminal (Hellman et al., 2011). The CXXC motif (residues 149-152 of human MANF, NCBI Reference Sequence: NP_006001.3) is located in the C-terminal domain (C-MANF) in the loop region outside the helical core of the domain, and the cysteines are connected with the disulfide bond (Hellman et al., 2011). Corresponding motif of CDNF is located at the same position (NCBI Reference Sequence: NP_001025125.2). It has been shown that C-MANF is potently anti-apoptotic in vitro, when expressed inside the sympathetic neurons (Hellman et al., 2011). In Lindström et al., 2013, characterization of structural and functional determinants of MANF and CDNF are disclosed.

Cell membranes with their selective permeability control molecular exchanges between the cytosol and the extracellular environment in a similar manner as the intracellular membranes do within the internal compartments. For this reason the plasma membranes often represent a challenging obstacle to the intracellular delivery of many molecules, especially high molecular weight molecules such as full-length proteins. The active transport of high molecular weight molecules through such barrier often requires specific carriers able to cross the lipid bilayer. Cell penetrating peptides (CPPs) are generally 5-30 amino acids long peptides (or motifs within a peptide) which, for their ability to cross cell membranes, are widely used to deliver proteins, plasmid DNA, RNA, oligonucleotides, liposomes and anticancer drugs inside the cells (Borrelli et al., 2018; Bode & Löwik, 2017; Kalafatovic & Giralt, 2017; Kristensen et al., 2016).

SUMMARY OF THE INVENTION

In the present invention, it has been discovered that a C-terminal fragment of the CDNF protein surprisingly protects ER stressed sympathetic and dopaminergic neurons in vitro and in vivo, and in contrast to full-length CDNF the fragment is capable of penetrating neuronal cell membrane as well as the blood-brain-barrier in vivo.

Accordingly, it is an aim of the present invention to provide a C-terminal CDNF fragment consisting of at least 50 consecutive amino acid residues of the sequence as set forth in SEQ ID NO: 1:

```
MPAMKICEKL KKLDSQICEL KYEKTLDLAS VDLRKMRVAE
LKQILHSWGE ECRACAEKTD YVNLIQELAP KYAATHPKTE L
```

or a sequence which preferably has at least 90% homology or sequence identity with the sequence of SEQ ID NO:1.

The present invention also provides a pharmaceutical composition comprising a C-terminal CDNF fragment and at least one of the following: physiologically acceptable carrier, buffer, excipient, preservative and stabilizer.

The results of the present invention further provides said C-terminal CDNF fragment for use in the treatment of a degenerative disease or disorder including a central nervous system (CNS) disease, diabetes or a retinal disease, wherein said CNS disease is preferably selected from the group consisting of Alzheimer's disease, Parkinson's disease, Huntington's disease and other amyloid diseases, multiple system atrophy, amyotrophic lateral sclerosis, frontotemporal lobar degeneration, dementia with Lewy bodies, mild cognitive impairment, traumatic brain injury, peripheral nerve injuries, addiction and stroke.

The present invention also shows that in contrast to the mature MANF protein the C-terminal fragment of MANF (C-MANF) is able to penetrate the cell membrane of dopamine neurons and protects the neurons in culture.

Another aim of the present invention is thus to provide a C-terminal MANF fragment, consisting of at least 50 consecutive amino acid residues of the sequence as set forth in SEQ ID NO: 2:

```
ICEKLKKKDS QICELKYDKQ IDLSTVDLKK LRVKELKKIL
DDWGETCKGC AEKSDYIRKI NELMPKYAPK AASARTDL
```

or a sequence which preferably has at least 90% homology or sequence identity with the sequence of SEQ ID NO:2 for use in the treatment of a degenerative disease or disorder including central nervous system (CNS) diseases, wherein said fragment is administered by intravenous or peripheral administration, intraperitoneal, subcutaneous, intranasal, transdermal, intramuscular, intraocular, or intra-arterial administration.

Also a pharmaceutical composition comprising said C-terminal MANF fragment, and at least one of the following: physiologically acceptable carrier, buffer, excipient and stabilizer, is provided for use in the treatment of a degenerative disease or disorder including central nervous system (CNS) diseases, wherein said fragment is administered by intravenous or peripheral administration, intraperitoneal, subcutaneous, intranasal, transdermal, intramuscular, intraocular, or intra-arterial administration.

Further aim of the present invention is to provide a C-terminal MANF fragment consisting of at least 50 consecutive amino acid residues of the sequence as set forth in SEQ ID NO:2:

```
ICEKLKKKDS QICELKYDKQ IDLSTVDLKK LRVKELKKIL
DDWGETCKGC AEKSDYIRKI NELMPKYAPK AASARTDL
```

or a sequence which preferably has at least 90% homology or sequence identity with the sequence of SEQ ID NO:2 for use in the treatment of type 1 or type 2 diabetes or a retinal disease.

The present invention also provides a pharmaceutical composition comprising the C-terminal MANF fragment and at least one of the following: physiologically acceptable carrier, buffer, excipient, preservative and stabilizer for use in the treatment of type 1 or type 2 diabetes or a retinal disease.

The aforementioned and other advantages and benefits of the present invention are achieved in the manner described as characteristics in the accompanying claims.

BRIEF DESCRIPTION OF THE DRAWINGS

FIG. 1.

FIG. 6A: $^{125}$I-C-CDNF, but not $^{125}$I-CDNF is efficiently internalized into E14 dopamine neurons in vitro showing cell penetrating properties of the C-CDNF. E14 dopamine neurons in culture were incubated with 30,000 cpm of iodinated CDNF or C-CDNF at 37° C. for 2 hr. The cells were then put on ice and washed with 0.2M acetic acid, 0.5M NaCl, pH 2.8 and counted in gamma counter. Radioactivity inside the cells was measured. FIG. 6B: $^{125}$I-C-CDNF and $^{125}$I-C-MANF, but not full length iodinated CDNF penetrate cell membrane of rat PC6 cells. Iodinated CDNF or C-CDNF and C-MANF were applied to PC6 cells that were treated with or without thapsigargin for 3 hours before the addition of growth factors. Internalization was let to occur at 37° for 90 min. The cells were put on ice and then washed with 0.2M acetic acid, 0.5M NaCl, pH 2.8 and radioactivity inside the cells was measured using gamma counter.

FIG. 12A: Relative changes in body weight, no gender classification. Week 12 (before the minipump installation) are shown as the baseline. Significant differences between treatments in body weight are detected in weeks 18 and 19 ($p<0,05$, two-tailed unpaired t-test). FIG. 12B: 4-week chronic intracerebroventricular C-CDNF infusion improves motor coordination as measured by rotarod performance in SOD1-G93A mice. In rotarod test an accelerating speed 4-40 rpm with a cut off time of 4 min was used. The difference between C-CDNF and PBS treatments was significant from week 13 until week 19 ($p<0.01$, repeated measures ANOVA).

FIG. 16A: Latency to fall. $p=0.01$ between QA+PBS and QA+C-CDNF, (repeated measurement two-way ANOVA).

FIG. 16B: Grip strength (left paw), 3w: $p=0.004$ between QA+PBS and QA+C-CDNF; 5w: $p=0.02$ between QA+PBS and QA+C-CDNF, (repeated measurement ANOVA). Adult Wistar rats received a single, unilateral intrastriatal injection of Quinolinic acid (QA). Quinolinic acid is a toxin that induces striatal neuron death by an excitotoxic process. C-CDNF improved motor performance in both rotarod and grip strength tests.

DETAILED DESCRIPTION OF THE INVENTION

The present invention is related to a neurotrophic factor protein CDNF. CDNF polypeptides are the full-length human CDNF with a signal peptide having the total length of 187 amino acids and the mature human CDNF without the signal peptide having the total length of 161 amino acids (see FIG. 1B).

The present invention is also related to neurotrophic factor protein MANF. Particularly important MANF polypeptides are the full-length human MANF with a signal peptide having the total length of 179 amino acids and the mature human MANF without the signal peptide having the total length of 158 amino acids (see FIG. 1B).

Figures 1A, 1B:
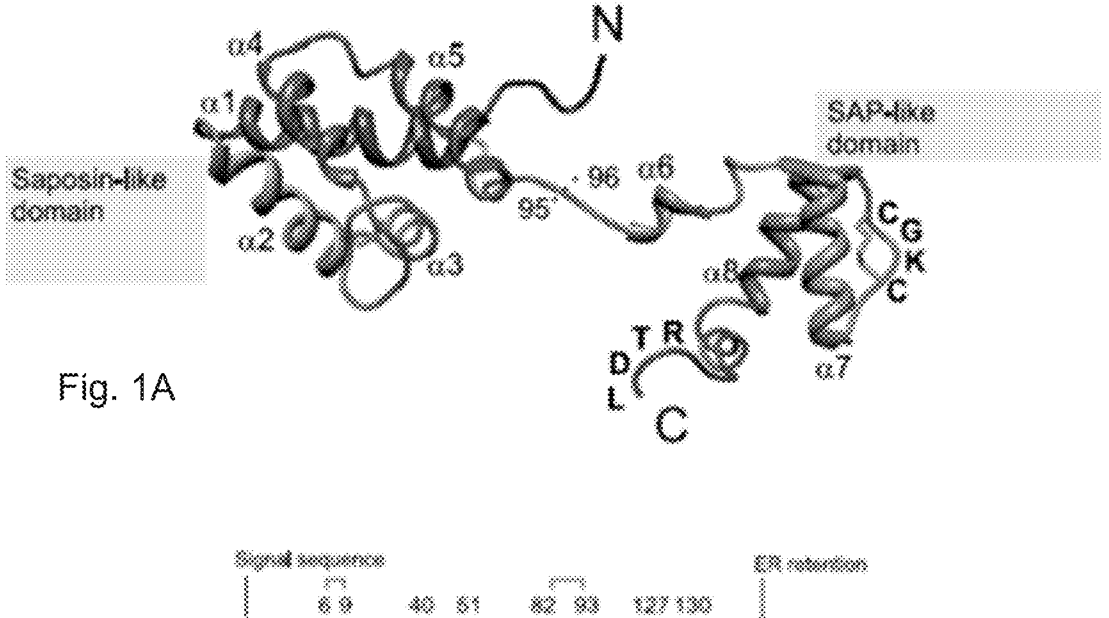
FIG. 1A: CDNF has two domains: The N-terminal domain and the C-terminal domain. N-terminal domain can bind oxidized phospholipids (and at least MANF N-terminal domain also lipid sulfatide, also known as 3-O-sulfogalactosylceramide, see Bai et al., 2018) and is a saposin-like domain. The C-terminal domain has the C-X-X-C(i.e. C-R-A-C, SEQ ID NO: 11) sequence and C-terminal ER retention signal KTEL and is a SAPLIP-like domain. CDNF can be proteolytically cleaved in vitro yielding these two domains.
FIG. 1B: Schematic view on the structures of MANF and CDNF. Black vertical bars show the location of 8 conserved cysteine residues.
Figure 2:
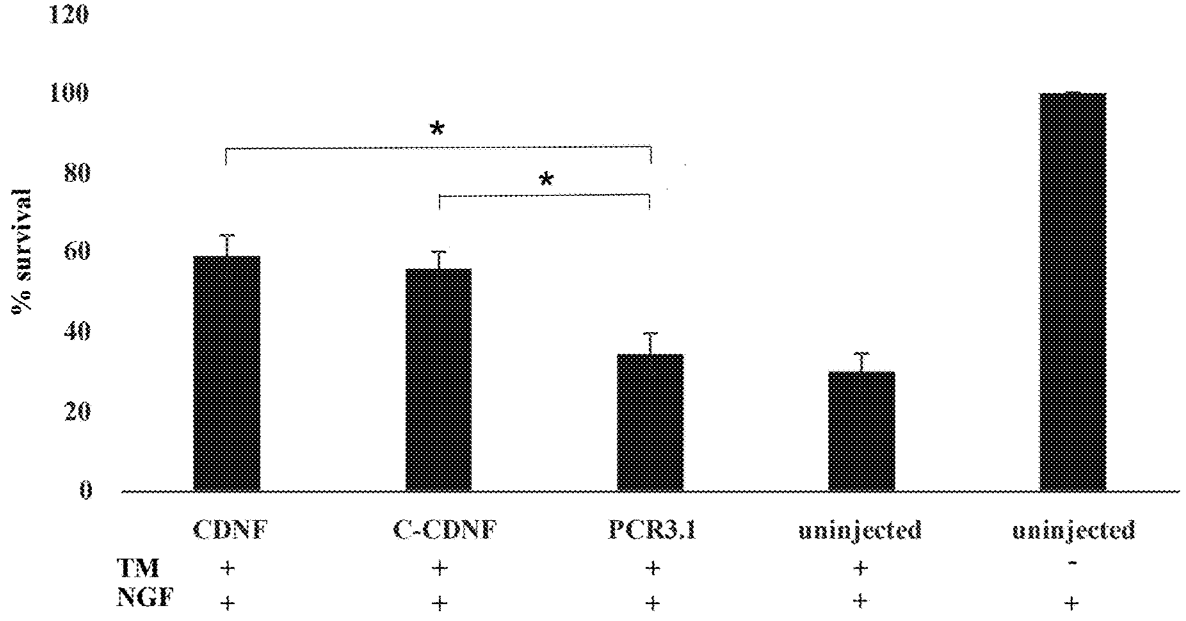
FIG. 2. CDNF and C-terminal fragment of CDNF expressed from plasmids rescue ER stressed superior cervical ganglia (SCG) sympathetic neurons. In the experiment, SCG neurons from 7 days old rats/mice were microinjected with indicated plasmids expressing CDNF, the C-terminal fragment of CDNF (C-CDNF), the control plasmid PCR3.1, and positive control when nerve growth factor (NGF at 10 ng/ml) was added to the culture medium. Next day tunicamycin™ at 2 μM was added to trigger ER stress-induced cell death, then after three days living and fluorescent neurons were counted and results are disclosed as percentage of initial neurons.
Figure 3:
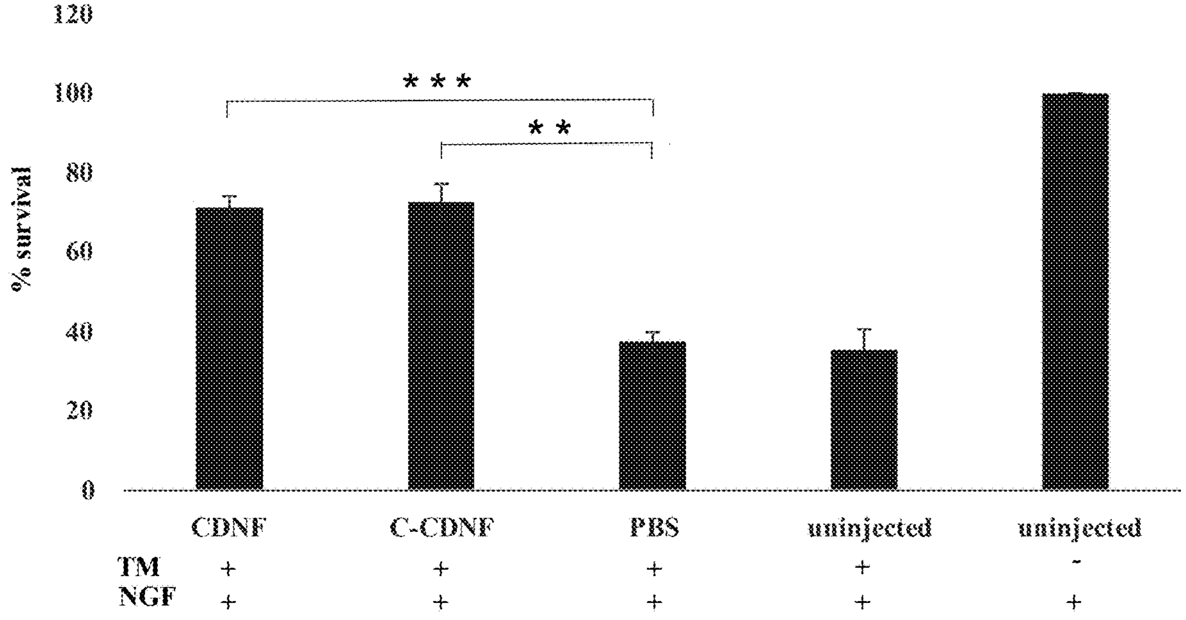
FIG. 3. CDNF and CDNF fragment proteins rescue ER stressed SCG neurons when microinjected into the cytoplasm. In the experiment, SCG neurons were prepared from postnatal day 1 old mice, cultured for 7 days, and then injected with the recombinant human CDNF or C-CDNF protein, respectively. Next day tunicamycin (2 μM) was added, and after 3 days the living fluorescent neurons were counted. The results are disclosed as a percentage of initial neurons.

As used herein, the term "C-terminal fragment" as applied to a CDNF or MANF polypeptide, may ordinarily comprise at least about 50 contiguous or consecutive amino acids, typically, at least about 55 contiguous or consecutive amino acids, more typically, at least about 57 or 60 contiguous or consecutive amino acids located in the C-terminal SAP-like domain of said polypeptides (See FIGS. 1A and 1B). The C-terminal fragment can also be longer than 61 or 65 contiguous or consecutive amino acids in length, in some cases more than 70 contiguous or consecutive amino acids. Most preferably, the C-terminal fragment comprises 57-61 or 60-65 contiguous or consecutive amino acids of the C-terminal domain. These C-terminal fragments are "functional fragments" retaining at least partly biological activity of the intact polypeptide and may even have properties the intact polypeptide does not have.

In addition to naturally occurring allelic variants of CDNF/MANF, changes can be introduced by mutation into CDNF/MANF nucleic acid sequences that incur alterations such as elongations, insertions and deletions in the amino acid sequences of the encoded CDNF/MANF polypeptide or C-terminal fragment thereof. Nucleotide substitutions leading to amino acid substitutions at "non-essential" amino acid residues can be made in the sequence of a CDNF/MANF polypeptide and the C-terminal domain thereof.

A "non-essential" amino acid residue is a residue that can be modified in the wild-type sequences of CDNF/MANF without altering its biological activity, whereas an "essential" amino acid residue is required for such biological activity. For example, amino acid residues that are conserved among the CDNF/MANF molecules of the invention are predicted to be essential and particularly non-amenable to alteration. Amino acids for which conservative substitutions can be made are well known in the art.

Each amino acid can be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrolysine. Non-natural amino acids can also be the D-isomer of the natural amino acids. Examples of suitable amino acids include, but are not limited to, alanine, alloisoleucine, arginine, asparagine, aspartic acid, cysteine, cyclohexylalanine, 2,3-diaminopropionic acid, 4-fluorophenylalanine, glutamine, glutamic acid, glycine, histidine, homoproline, isoleucine, leucine, lysine, methionine, naphthylalanine, norleucine, phenylalanine, phenylglycine, pipecolic acid, proline, pyroglutamic acid, sarcosine, serine, selenocysteine, threonine, tryptophan, tyrosine, valine, a derivative, or combinations thereof.

Certain embodiments of the invention include C-terminal CDNF fragments or C-terminal MANF fragments wherein at least one, two, three, four or more consecutive amino acids have alternating chirality. As used herein, chirality refers to the "D" and "L" isomers of amino acids. In particular embodiments of the invention, at least one, two, three, four or more consecutive amino acids have alternating chirality and the remaining amino acids are L-amino acids.

In present disclosure, the cellular uptake of the C-terminal CDNF fragments and C-terminal MANF fragments of the invention into neuronal cells has been demonstrated. In certain embodiments, uptake is preferably at least 2, 3, 4, 5, 6, 7, 8, 9, 10, 11, or 12 times better compared to full length CDNF or MANF, and with specific peptides even 13 times better than full-length CDNF or MANF. In certain embodiments, the invention demonstrates improved cellular uptake efficiency of the C-terminal CDNF fragments of the invention as compared to controls such as full-length human CDNF. In certain embodiments, the invention demonstrates improved cellular uptake efficiency of the C-terminal MANF fragments of the invention as compared to controls such as full-length human MANF.

As used herein cellular uptake efficiency refers to the ability of a C-terminal CDNF fragment or C-terminal MANF fragment to traverse a cell membrane. Cellular uptake of the C-terminal CDNF fragments or C-terminal MANF fragments of the invention is not dependent on a receptor or a cell type.

A person skilled in the art can test uptake efficiency of a C-terminal CDNF fragment and/or C-terminal MANF fragment by comparing (i) the amount of a cell-penetrating peptide such as the C-terminal CDNF fragments or C-terminal MANF fragments internalized by a cell type (e.g., neuronal cells, endothelial cells) to (ii) the amount of a control peptide such as full-length CDNF/MANF internalized by the same cell type. To measure cellular uptake efficiency, the cell type may be incubated in the presence of a cell-penetrating peptide such as the C-terminal CDNF fragment or C-terminal MANF fragment for a specified period of time (e.g., 30 minutes, 1 hour, 2 hours, etc.) after which the amount of the cell-penetrating peptide internalized by the cell is quantified. Separately, the same concentration of the control is incubated in the presence of the cell type over the same period of time, and the amount of the second peptide internalized by the cell is quantified. Quantification can be achieved by fluorescently labeling the cell-penetrating peptide such as the C-terminal CDNF fragments or C-terminal MANF fragments (e.g., with a FITC dye) and measuring the fluorescence intensity using techniques well-known in the art.

The C-terminal CDNF fragments and C-terminal MANF fragments of the invention also demonstrate protective effect for cells, e.g. neuronal cells as compared to suitable controls. As used herein protective effect refers to the ability of a C-terminal CDNF fragments or C-terminal MANF fragments of the invention to promote survival of, e.g., dopaminergic neurons or ER stressed neuronal cells. A person skilled in the art can test said protective effect by comparing (i) the dose of a C-terminal CDNF fragments or C-terminal MANF fragments of the invention to survival of a cell type (e.g., sympathetic neuronal cells or dopaminergic neurons) to (ii) the level of survival of control peptide by the same cell type or to the level of survival of no added neurotrophic factors by the same cell type. To measure cell survival, the cell type may be incubated in the presence of a C-terminal CDNF fragments or C-terminal MANF fragments of the invention for a specified period of time (e.g., 30 minutes, 1 hour, 2 hours, etc.) after which the cell survival of the cell is quantified. Separately, the same concentration of control peptide is incubated in the presence of the cell type over the same period of time, and the cell survival of the second peptide by the cell is quantified. Alternatively, the cell type is incubated without neurotrophic factors over the same period of time, and the cell survival by the cell is quantified.

In an embodiment, to measure cell survival, the cell type may be injected with a C-terminal CDNF fragments or C-terminal MANF fragments of the invention and incubated for a specified period of time (e.g., 30 minutes, 1 hour, 2 hours, etc.) after which the cell survival of the cell is quantified. Control cells are injected with a buffer (i.e. with no neurotrophic factors) and the control cells are incubated over the same period of time, and the cell survival by the cell is quantified.

In certain embodiments, protective effect (measured as cell survival) of the C-terminal CDNF fragment of the invention is at least 1.09-fold, at least 1.20-fold, at least 1.24-fold, at least 1.85-fold, at least 1.96-fold, at least 2.11-fold or at least 2.20-fold compared to the cells incubated in presence of no added growth factors or injected with a buffer without growth factors.

In an embodiment, the protective effect is at least 1.09-fold to the cells incubated in presence of no added growth factors or injected with a buffer without growth factors.

In an embodiment, the protective effect is at least 1.20-fold to the cells incubated in presence of no added growth factors or injected with a buffer without growth factors.

In an embodiment, the protective effect is at least 1.24-fold to the cells incubated in presence of no added growth factors or injected with a buffer without growth factors.

In an embodiment, the protective effect is at least 1.85-fold to the cells incubated in presence of no added growth factors or injected with a buffer without growth factors.

In an embodiment, the protective effect is at least 1.96-fold to the cells incubated in presence of no added growth factors or injected with a buffer without growth factors.

In an embodiment, the protective effect is at least 2.11-fold to the cells incubated in presence of no added growth factors or injected with a buffer without growth factors.

In an embodiment, the protective effect is at least 2.20-fold to the cells incubated in presence of no added growth factors or injected with a buffer without growth factors.

In certain embodiments, protective effect of the C-terminal MANF fragment of the invention is at least 1.18-fold compared to the cells incubated in presence of no added growth factors or injected with a buffer without growth factors.

Accordingly, the present invention provides a C-terminal CDNF fragment consisting of at least 50 consecutive amino acid residues of the sequence as set forth in SEQ ID NO:1:

```
MPAMKICEKL KKLDSQICEL KYEKTLDLAS VDLRKMRVAE
LKQILHSWGE ECRACAEKTD YVNLIQELAP KYAATHPKTE L
```

or a sequence which is at least 90% homologous to the sequence of SEQ ID NO:1.

The present invention is also related to a C-terminal MANF fragment consisting of at least 50 consecutive amino acid residues of the sequence as set forth in SEQ ID NO:2:

```
ICEKLKKKDS QICELKYDKQ IDLSTVDLKK LRVKELKKIL
DDWGETCKGC AEKSDYIRKI NELMPKYAPK AASARTDL
```

or a sequence which is at least 90% homologous to the sequence of SEQ ID NO:2.

As used herein in the specification and in the claims section below, the term "fragment" includes native peptides (either degradation products, synthetically synthesized peptides or recombinant peptides) and modified peptides, which may have, for example, modifications rendering the peptides more stable or less immunogenic. Such modifications include, but are not limited to, cyclization, N-terminus modification, C-terminus modification, peptide bond modification, backbone modification and residue modification. The fragment may also comprise further elongations, deletions or insertions.

In the embodiments of the invention, the length of the fragment is in the range of 50-81 amino acids. Preferably, the length of the fragment is in the range of 55-75, 55-70, 55-61, 61-65, or 61-70 amino acids. More preferably, the length of the fragment is in the range of 57-61, 55-69, 55-68, 55-67, 55-66, 56-69, 56-68, 56-67, 56-61, 57-69, 57-68, 57-67, 57-61, 58-69, 58-68, 58-67, 58-61, 59-69, 59-68, 59-67, 59-61, 60-69, 60-68, 60-67, 60-66, 60-64, 60-63, 61-62, 61-63, 61-64, 61-65, 61-66, or 61-67 amino acids. For example, the preferred fragments can consist of at least 55, 56, 57, 58, 59, 60, 61, 62, 63, 64, 65, 66, 67, 68, 69, 70, 71, 72, 73, 74 or 75 amino acids. The fragments may comprise any of the naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine as well as non-conventional or modified amino acids. Preferably, the fragment has at least 100%, 99%, 98%, 97%, 96%, 95%, 94%, 93%, 92%, 91%, 90%, 85%, or 80% homology or sequence identity with the sequence of the C-terminal domain in the human CDNF or MANF protein. More preferably, the fragment has at least 80% homology or sequence identity with the sequence of the C-terminal domain in the human CDNF or MANF protein. "Homology" or "homologous" as used herein refers to sequence similarity between a reference sequence and at least a fragment of a second sequence. As described below, BLAST will compare sequences based upon percent identity and similarity.

The terms "identical" or percent "identity," in the context of two or more amino acid sequences, refers to two or more sequences or subsequences that are the same. Two sequences are "substantially identical" if two sequences have a specified percentage of amino acid residues that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 10 amino acids in length, or more preferably over a region that is 10, 15, 20, 25, 30 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity.

A "comparison window," as used herein, includes reference to a segment of any one of the number of contiguous positions in which a sequence may be compared to a reference sequence of the same number of contiguous positions after the two sequences are optimally aligned. Methods of alignment of sequences for comparison are well known in the art such as ClustalW or FASTA.

Two examples of algorithms that are suitable for determining percent sequence identity and sequence similarity are the BLAST and BLAST 2.0 algorithms, which are described in Altschul et al. (1997) Nucleic Acids Res 25 (17): 3389-3402 and Altschul et al. (1990) J. Mol Biol 215

(3)-403-410, respectively. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89 (22): 10915-10919] alignments (B) of 50, expectation (E) of 10, M=5, N=−4, and a comparison of both strands. For short amino acid sequences, PAM30 scoring matrix can be applied.

The BLAST algorithm also performs a statistical analysis of the similarity between two sequences (see, e.g., Karlin and Altschul, (1993) Proc Natl Acad Sci USA 90 (12): 5873-5877). One measure of similarity provided by the BLAST algorithm is the smallest sum probability (P(N)), which provides an indication of the probability by which a match between two amino acid sequences would occur by chance.

Preferably, the C-terminal CDNF which is at least 90% homologous to the sequence of SEQ ID NO: 1 comprises sequence CXXC in positions 52-55 of SEQ ID NO:1, wherein X is any amino acid. More preferably, said sequence which is at least 90% homologous to the sequence of SEQ ID NO: 1 consists of at least 50 consecutive amino acid residues of the sequence of SEQ ID NO:3:

```
MPAMKICEKL KKLDSQICEL KYEKTLDLAS VDLRKMRVAE

LKQILHSWGE ECXXCAEKTD YVNLIQELAP KYAATHPKTE L
```

wherein X is any amino acid.

In another preferred embodiment, said sequence which is at least 90% homologous to the sequence of SEQ ID NO: 1 comprises sequence CKGC (SEQ ID NO:12) in positions 52-55 of SEQ ID NO:1

In the most preferred embodiment, said fragment has the sequence of SEQ ID NO:4:

```
KYEKTLDLAS VDLRKMRVAE LKQILHSWGE ECRACAEKTD

YVNLIQELAP KYAATHPKTE L
```

or a sequence which has at least 90% homology or sequence identity to the sequence of SEQ ID NO: 4.

In an embodiment, the C-terminal CDNF fragment does not contain its natural C-terminal amino acids, i.e. the ER retention signal. Accordingly, in a preferred embodiment the fragment lacks the ER retention signal KTEL (SEQ ID NO:13) corresponding to positions 78-81 of SEQ ID NO:1.

The present invention also shows that the fragment may be conjugated to a detectable chemical or biochemical moiety such as a FITC-label. As used herein, a "detectable chemical or biochemical moiety" means a tag that exhibits an amino acid sequence or a detectable chemical or biochemical moiety for the purpose of facilitating detection of the peptide; such as a detectable molecule selected from among: a visible, fluorescent, chemiluminescent, or other detectable dye; an enzyme that is detectable in the presence of a substrate, e.g., an alkaline phosphatase with NBT plus BCIP or a peroxidase with a suitable substrate; a detectable protein, e.g., a green fluorescent protein. Preferably, the tag does not prevent or hinder the penetration of the fragment into a target cell.

N- and/or C-terminal modifications of the C-terminal CDNF fragments or C-terminal MANF fragments to increase the stability and/or cell permeability of the fragments are also preferred. Acetylation—amidation of the termini of the CDNF fragment or MANF fragment (i.e. N-terminal acetylation and C-terminal amidation) is one of the options known in the art (see e.g. Marino et al. 2015, ACS Chem. Biol. 10:1754-1764).

Figure 4:
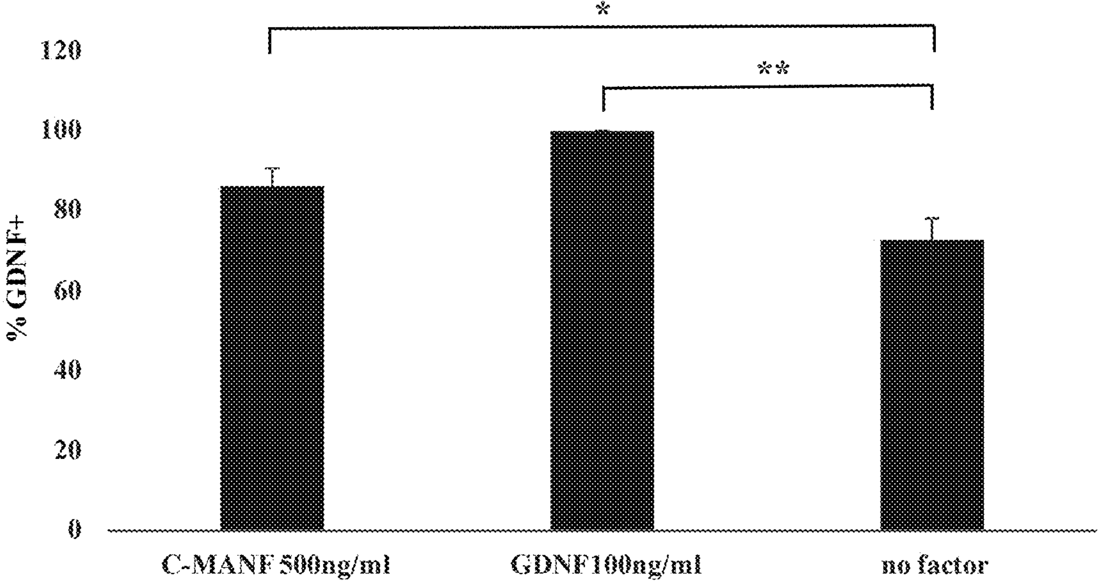
FIG. 4. C-terminal fragment of MANF (C-MANF) protects dopaminergic neurons in culture. Dissociated cultures of embryonic day 13 (E13) NMRI mouse midbrain floors were grown on a 96-well plate for 5 days with C-MANF, GDNF added to the culture medium (positive control) or without growth factors as control. The cultures were thereafter stained for tyrosine hydroxylase (TH). Images were scanned by CellInsight™ and immunopositive neurons counted by CellProfiler and CellProfiler analyst software. Data are expressed as a percentage of GDNF-maintained TH-positive neurons.
Figure 5:
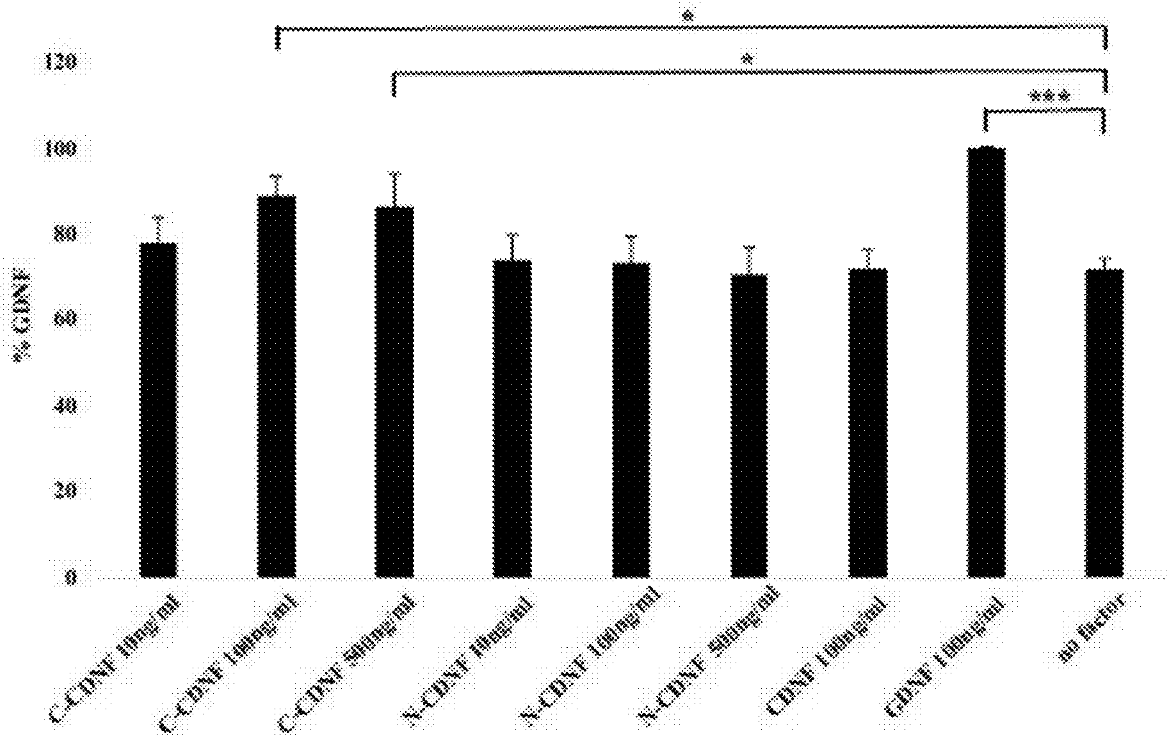
FIG. 5. The C-terminal fragment of CDNF (C-CDNF) protects dopaminergic neurons in vitro. Dissociated cultures of E13.5 NMRI mouse midbrain floors were grown on the 96-well plate for 5 days with CDNF or CDNF fragments added to the culture medium at given concentrations. Dopamine neurons cultured with GDNF (100 ng/ml) or without neurotrophic factors served as controls. The cultures were immunostained for tyrosine hydroxylase (TH), images were scanned by CellInsight™. TH-positive neurons were counted by CellProfiler and CellProfiler analyst software and expressed as a percentage of GDNF-maintained neurons.
Figure 8:
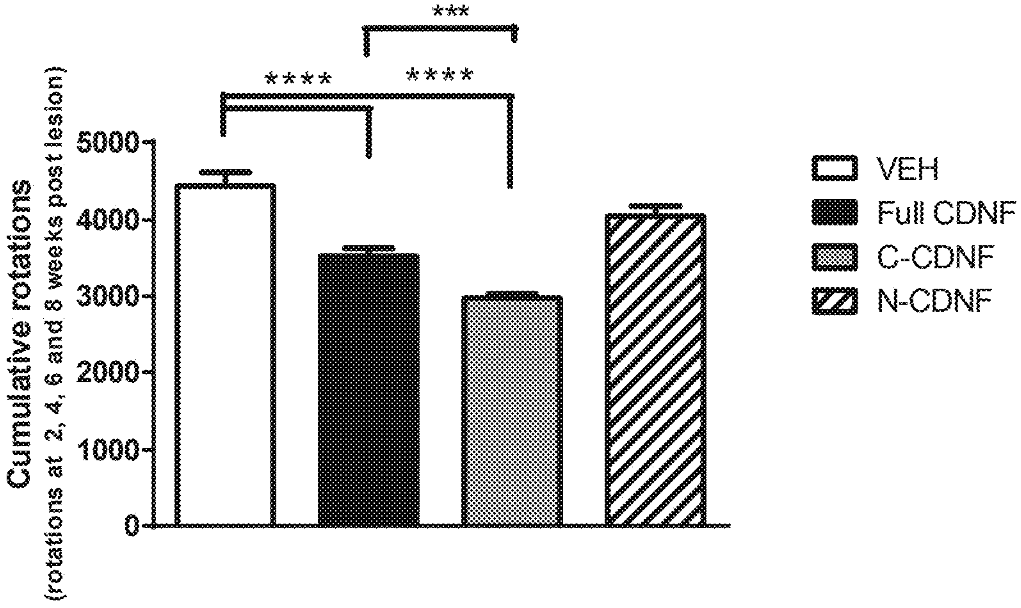
FIG. 8. Cumulative rotations at 2, 4, 6 and 8 weeks post-lesion in the rat 6-OHDA model of PD. CDNF, N terminal CDNF fragment (N-CDNF), C-CDNF or vehicle (PBS) were injected intrastriatally into rat brain 2 weeks after 6-OHDA lesioning. C-CDNF is more efficacious than full length CDNF in restoring neuronal function as it significantly reduces the cumulative amount of amphetamine-induced rotations in 6-OHDA lesioned rats. Data are shown as mean±SEM. Tukey-Kramer's post hoc analysis after one-way ANOVA, **** $p<0.0001$ FIGS. 9A-B. Short, 4-amino acids long C-terminal fragment of MANF (MANF4) is not effective in the rat 6-OHDA model of Parkinson's disease when the peptide is infused into the striatum starting 2 weeks after 6-OHDA lesioning and amphetamine-induced rotations measured at 1, 4, 6, 8, 10 and 12 weeks post lesioning (FIG. 9A) or cumulatively (FIG. 9B). GDNF was used as positive control.
Figure 9A:
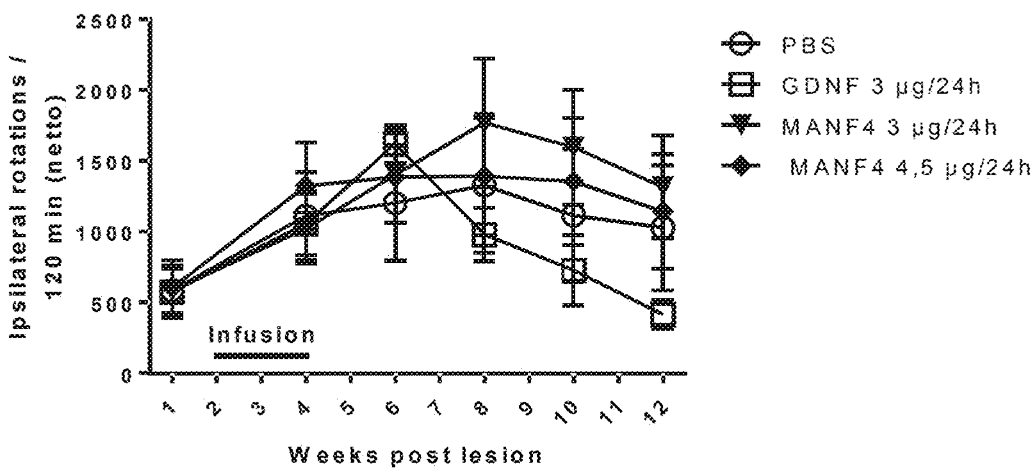
Figure 9B:
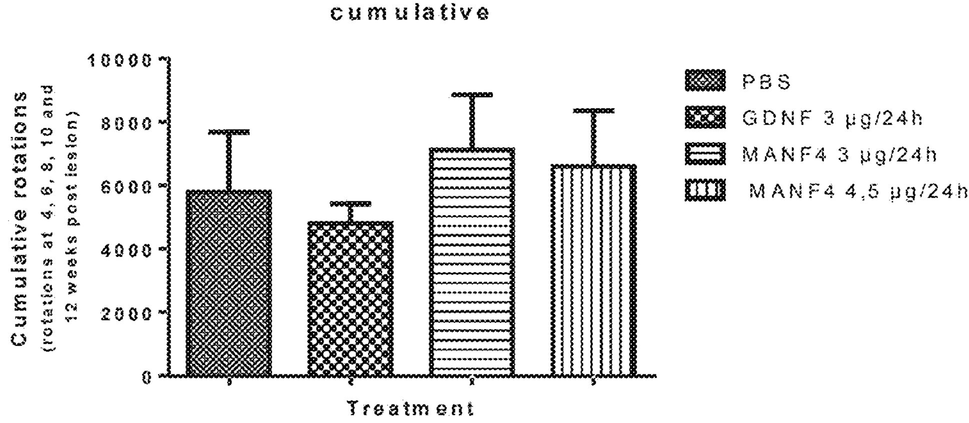
Figure 11A:
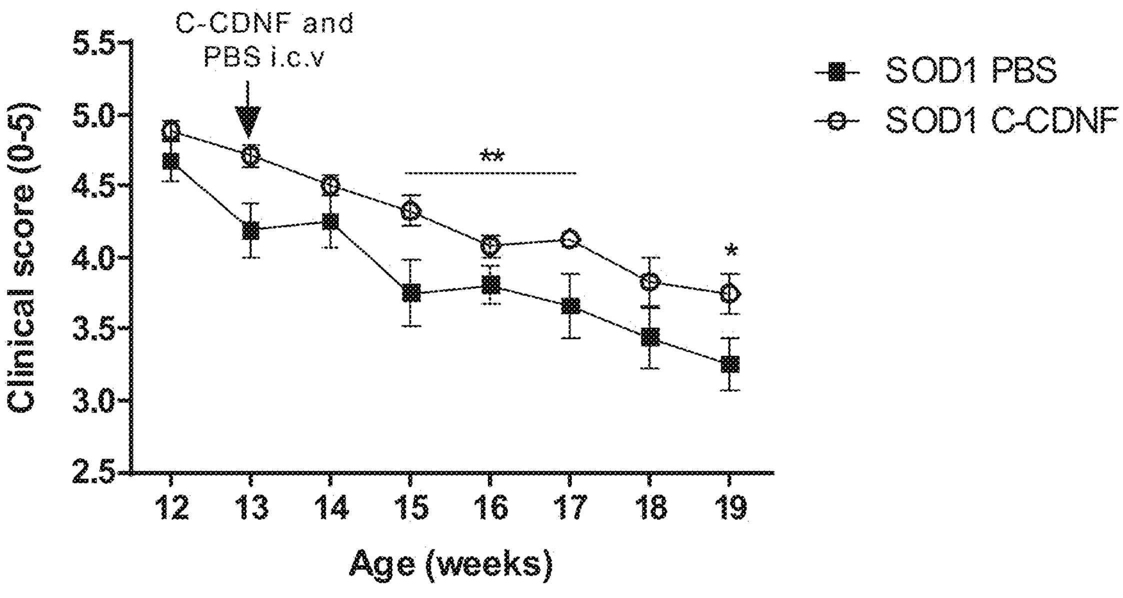
FIG. 11A: Clinical status of female animals. C-CDNF treatment slows down the symptom onset as C-CDNF treated SOD1 mice had statistically significantly better clinical scores than PBS-treated mice.
Figure 11B:
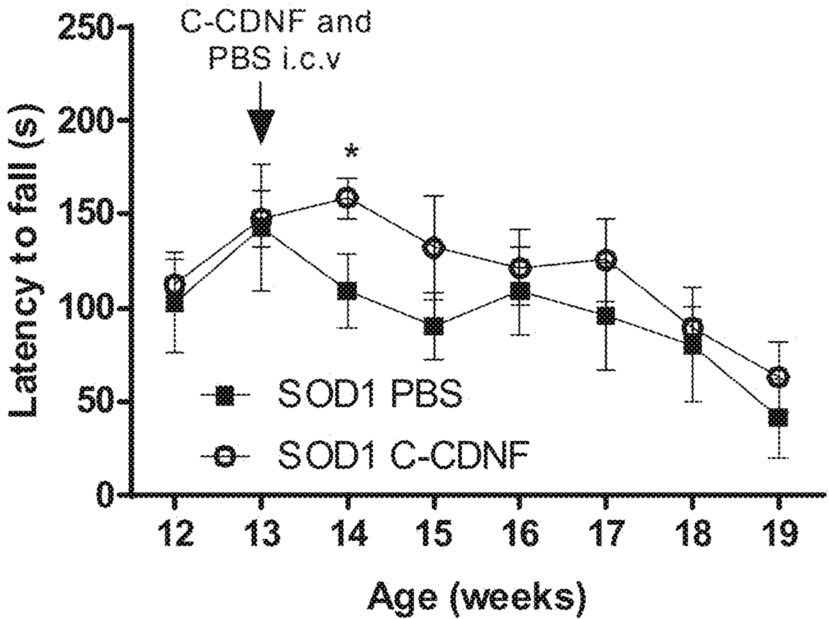
FIG. 11B: Balance, coordination and muscle strength were assayed with rotarod. Accelerated speed 4-40 rpm, cut-off time 4 min. Latency to fall(s) is shown on the left. SOD1-G93A females. C-CDNF treatment improves the motor behavior of SOD1-G93A mice compared to PBS treated mice.
Figures 12A, 12B:
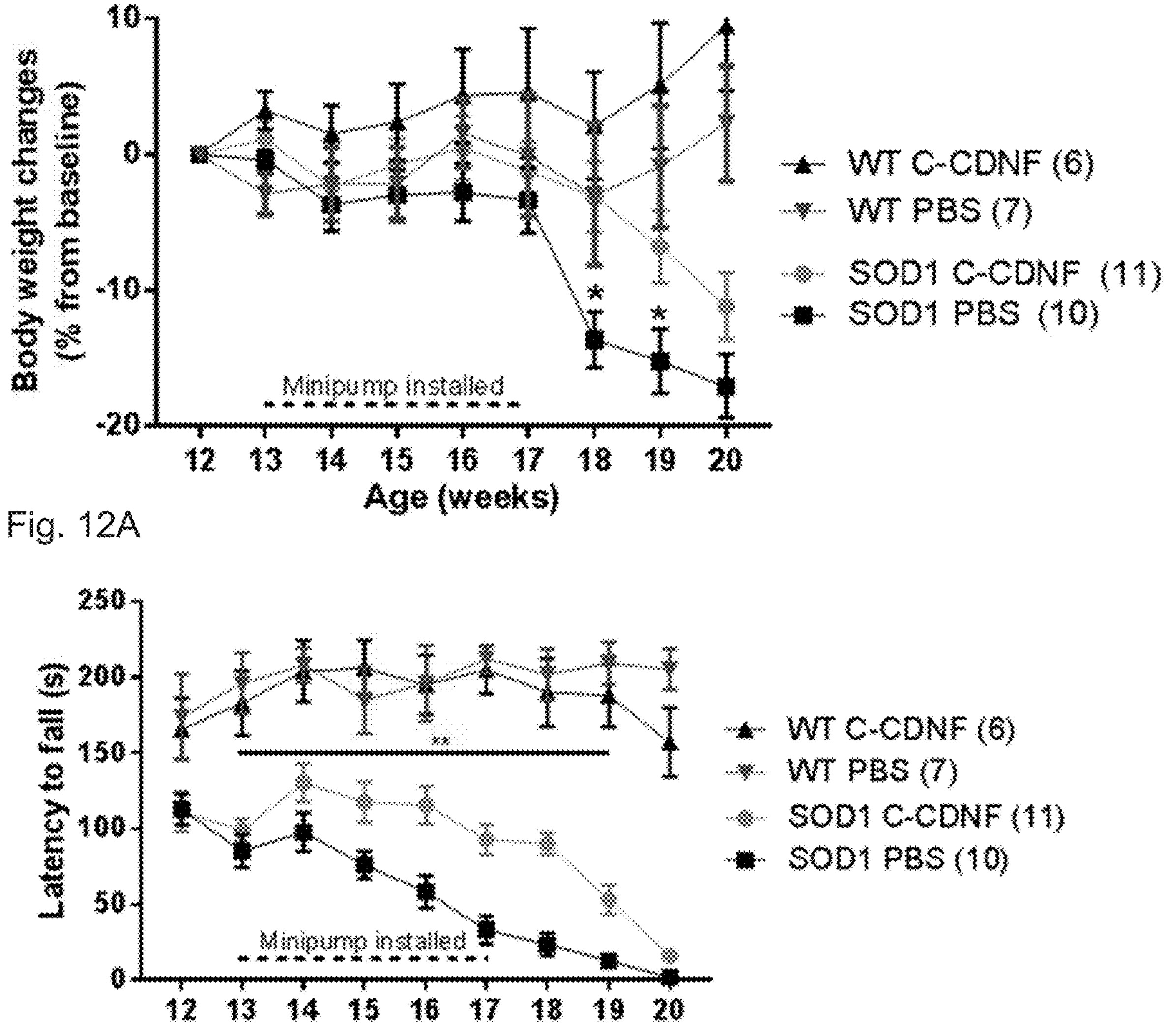
FIGS. 12A-B. Effect of 4-week chronic intracerebroventricular infusion of C-CDNF at 1.5 μg/24 h in SOD1-G93A mouse ALS model.

Since both the C-terminal CDNF fragment and the C-terminal MANF fragment potently protected the dopamine neurons from death (see FIGS. 4 and 5), the prior art such as WO2009133247, and EP1969003 shows that the fragments can be used in the treatment of central nervous system (CNS) diseases such as Alzheimer's disease, Parkinson's disease (PD), multiple system atrophy, amyotrophic lateral sclerosis (ALS), frontotemporal lobar degeneration, dementia with Lewy bodies, mild cognitive impairment, Huntington's disease (HD), traumatic brain injury, drug addiction and stroke. Further results supporting the present invention are provided in FIG. 8 showing the effect of C-CDNF in a PD model and in FIGS. 11 and 12 showing the effect of C-CDNF in an ALS model. It is also notable that a short MANF peptide (MANF4) is not effective in the rat 6-OHDA model of Parkinson's disease when tested in neurorestorative, more clinically oriented set up i.e. when added after 6-OHDA (see FIG. 9).

The effects of C-terminal CDNF fragment or the C-terminal MANF fragment in CNS include targeting neurons but also other cell types in the CNS such as microglia, astrocytes and neural stem cells or a neuronal precursor cell, and besides survival also any other property they have such as migration, proliferation, differentiation and maturation.

Figure 10:
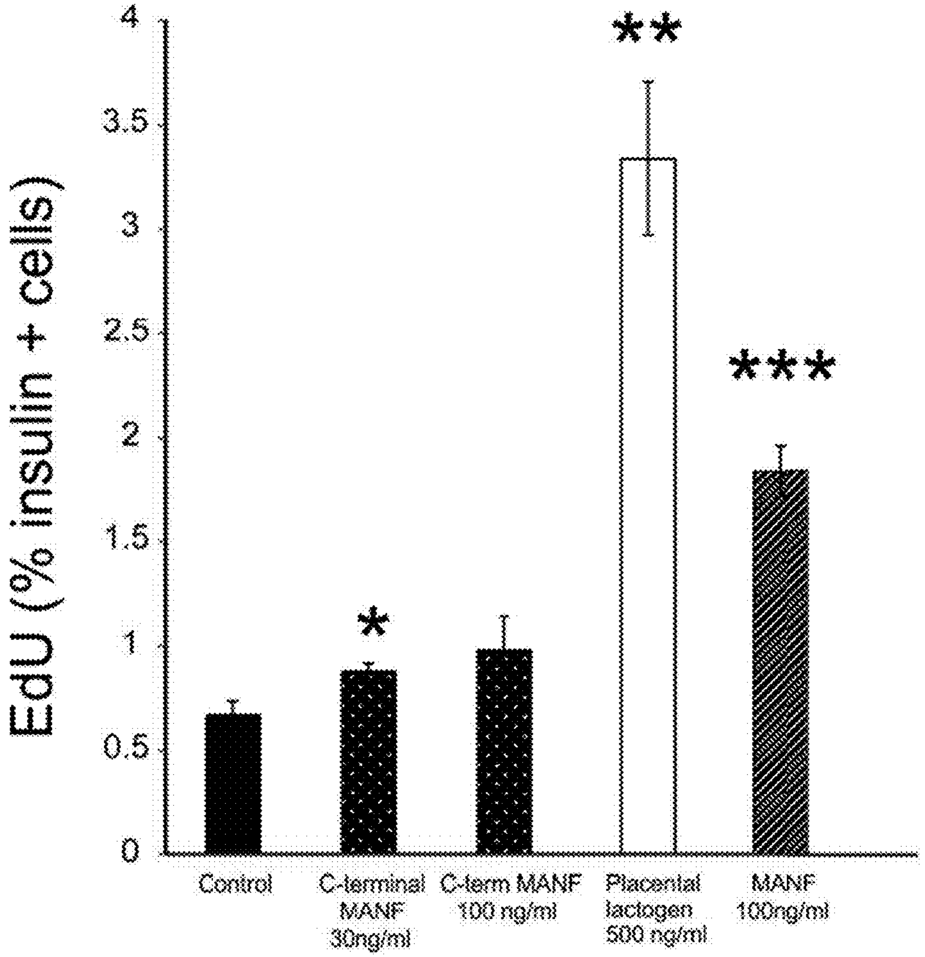
FIG. 10. The C-terminal MANF fragment (C-MANF) stimulates mouse beta cell proliferation. Incorporation of Click EdU in beta cells after in vitro culturing of mouse islets for 5 days with placental lactogen, C-MANF or MANF (n=3 wells/point). * $p<0.05$,  $p<0.01$, * $p<0.001$ FIGS. 11A-B. Treatment with C-CDNF has beneficial effects on clinical score in superoxie dismutase (SOD) 1 mouse model of ALS. SOD1-G93A mice were given a single intracerebroventricular injection of C-CDNF (3.75 μg) or PBS at the age of 13 weeks.

Our results shown in FIG. 10 confirm that the C-terminal MANF fragment is effective in the treatment of type I and type II diabetes. Further, WO2016057579 discloses that CDNF and MANF are also active in retinal disorders. Accordingly, the present invention is directed to a treatment of said central nervous system (CNS) diseases, diabetes and retinal disorders. ER-stress-induced apoptotic cell death also contribute to other degenerative diseases in which the function or structure of the affected tissues or organs will progressively deteriorate over time (for a review, see Oakes and Papa, Annu. Rev. Pathol. Mech. Dis. 2015. 10:173-94). Some further examples of such degenerative diseases are age-related macular degeneration, Stargardt disease, glaucoma, retinitis pigmentosa, and optic nerve degeneration; Niemann-Pick disease; atherosclerosis; progressive supranuclear palsy; cancer; Tay-Sachs disease; keratoconus; inflammatory bowel disease (IBD); prostatitis; osteoarthritis; osteoporosis; and rheumatoid arthritis as well as more acute conditions such as a traumatic brain injury or an ischemia-reperfusion injury, e.g., myocardial ischemic injury, renal ischemic injury, or stroke. The present invention is thus also directed to a treatment of a degenerative disease or disorder.

In a method of treatment, a pharmaceutically effective amount of the C-terminal fragment is administered to a patient. In other words, the fragment according to the present invention is for use in the treatment of a degenerative disease or disorder including central nervous system (CNS) diseases and other neurological disorders such as Alzheimer's disease, Parkinson's disease (PD), non-motor symptoms of PD (such as constipation, depression and hallucinations), multiple system atrophy, amyotrophic lateral sclerosis, ischemic stroke, peripheral neuropathy, frontotemporal lobar degeneration, dementia with Lewy bodies, mild cognitive impairment, Huntington's disease, epilepsy, traumatic brain injury, peripheral nerve injuries, hemorrhagic stroke or addiction (e.g., abuse of cocaine, morphine, amphetamine, or alcohol), and type I and type II diabetes or retinal disorders. More preferably, the fragment is for use in the treatment of Parkinson's disease or amyotrophic lateral sclerosis.

The actual dosage amount of the C-terminal fragment of CDNF or MANF (e.g., an effective amount) that is administered to a patient can be determined by physical and physiological factors such as body weight, severity of condition, the type of disease being treated, previous or concurrent therapeutic interventions, idiopathy of the patient and on the route of administration. The practitioner responsible for administration can determine the concentration of active ingredient(s) in a composition and appropriate dose(s) for the individual subject.

In one embodiment of the present invention, the C-terminal CDNF fragment or MANF fragment can be incorporated into pharmaceutical compositions. Such compositions of the invention are prepared for storage by mixing the peptide having the desired degree of purity with optional physiologically acceptable carriers (such as nanocarriers), excipients, or stabilizers (Remington's Pharmaceutical Sciences, 22nd edition, Allen, Loyd V., Jr, Ed., (2012)), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

The fragment may also be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

In an embodiment, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

In other non-limiting examples, a dose of a pharmaceutical composition or formulation can comprise from about 1 ng/kg/body weight of C-terminal CDNF fragment or C-terminal MANF fragment, about 5 ng/kg/body weight, about 10 ng/kg/body weight, about 50 ng/kg/body weight, about 100 ng/kg/body weight, about 200 ng/kg/body weight, about 350 ng/kg/body weight, about 500 ng/kg/body weight, 1 μg/kg/body weight, about 5 μg/kg/body weight, about 10 μg/kg/body weight, about 50 μg/kg/body weight, about 100 μg/kg/body weight, about 200 μg/kg/body weight, about 350 μg/kg/body weight, about 500 μg/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight of C-terminal CDNF fragment or C-terminal MANF fragment or more per administration, and any range derivable therein. In non-limiting examples of a derivable range from the numbers listed herein, a range of about 5 mg/kg/body weight to about 100 mg/kg/body weight, about 5 μg/kg/body weight to about 500 milligram/kg/body weight of C-terminal CDNF fragment or C-terminal MANF fragment, etc., can be administered, based on the numbers described above.

The invention also features a pharmaceutical composition that can further include a neural cell. The neural cell can be, for example, a neuron, a neural stem cell, or a neuronal precursor cell.

In another embodiment, the pharmaceutical composition comprises a therapeutically effective amount of recombinant vectors comprising a nucleotide sequence that encodes a C-terminal fragment as defined above, recombinant viral vectors comprising a nucleotide sequence that encodes a C-terminal fragment as defined above, or a host cell expressing a C-terminal fragment as defined above. Said viral vector is preferably selected from the group consisting of an adenovirus, an adeno-associated virus, a retrovirus such as a lentivirus, herpes virus, and papillomavirus comprising a polynucleotide encoding a C-terminal fragment as defined above. Typically the recombinant vectors and recombinant viral vectors include expression control sequences like tissue- or cell-type specific promoters that direct the expression of the polynucleotide of the invention in various systems, both in vitro and in vivo. Vectors can also be hybrid vectors that contain regulatory elements necessary for expression in more than one system. Vectors containing these various regulatory systems are commercially available and one skilled in the art will readily be able to clone the C-terminal fragment as defined herein into such vectors. Selection of recombinant viral vectors suitable for use in the invention, methods for inserting nucleic acid sequences for expressing the C-terminal fragment into the vector, and methods of delivering the viral vector to the cells of interest are within the skill in the art. See, for example, Dornburg R (1995), Gene Therap. 2:301-310.

Figure 6A:
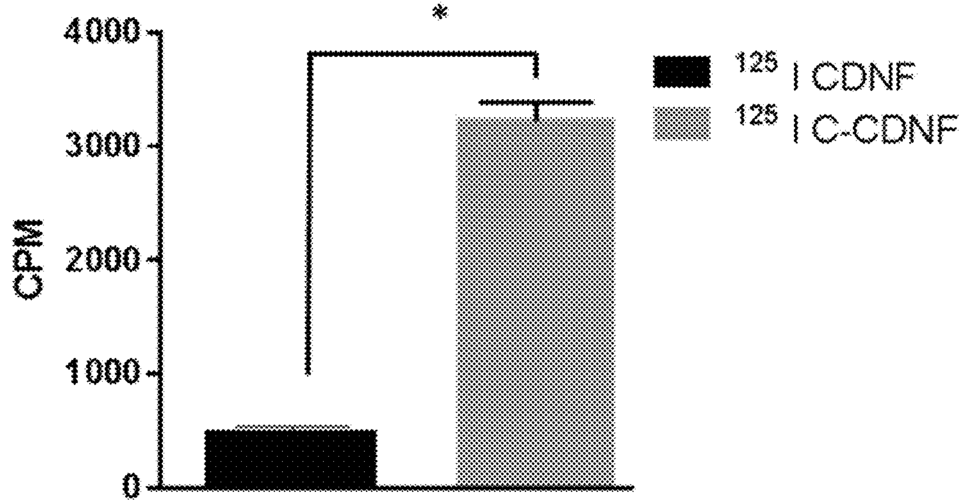
FIGS. 6A-6B. The C-terminal fragment of CDNF (C-CDNF) and C-terminal fragment of MANF (C-MANF) penetrates cell membrane of dopamine neurons and PC6 cells.
Figure 6B:
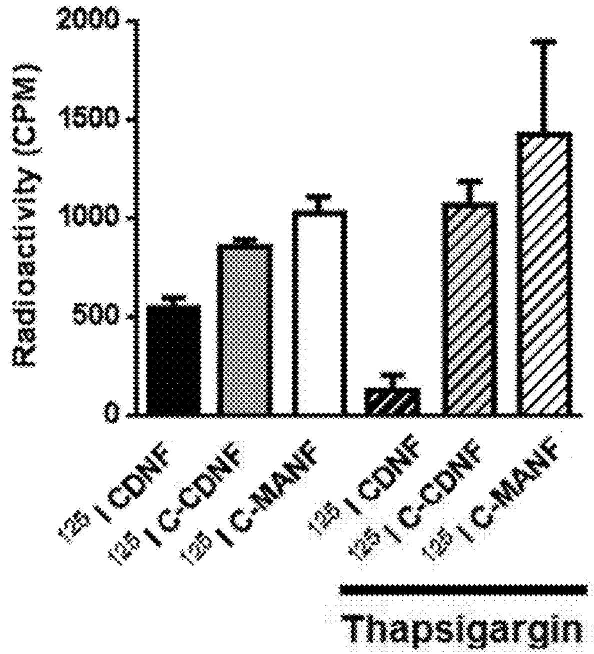
Figure 7:
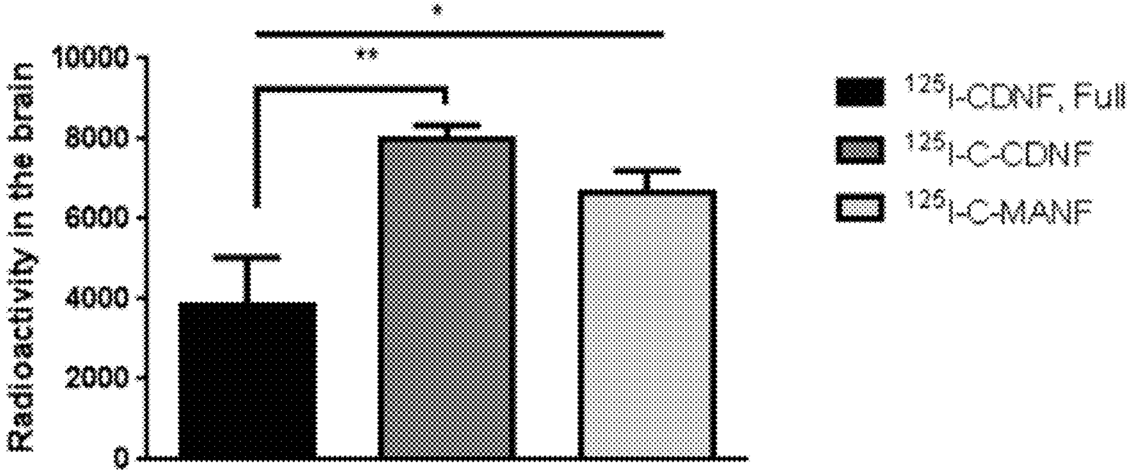
FIG. 7. Blood-brain-barrier penetration of $^{125}$I-CDNF, $^{125}$I-C-CDNF and $^{125}$I-C-MANF. $^{125}$I-CDNF, $^{125}$I-C-CDNF and $^{125}$I-C-MANF were injected subcutaneously to rats. Rats were perfused with PBS 2 hours later and the brain dissected out. Radioactivity in brain was analyzed by gamma counter. Data are shown as mean±SEM, ** $p<0.01$, * $p<0.05$ post hoc comparison followed by one-way ANOVA.

The route of administration is in accord with known methods as well as the general routes of injection or infusion by intravenous or peripheral administration, intraperitoneal, subcutaneous, intrathecal, intracerebroventricular, intranasal, transdermal, intracerebral, intramuscular, intraocular, intraarterial, or intralesional means, or sustained release systems as noted below. The C-terminal fragment or a pharmaceutical composition comprising said fragment can be administered continuously by infusion or by bolus injection. Generally, where the disorder permits, one should formulate and dose the fragment for site-specific delivery. Administration can be continuous or periodic. Administration can be accomplished by a constant- or programmable-flow implantable pump or by periodic injections. Peripheral or systemic administration is preferred as the present invention shows that both C-terminal MANF and CDNF fragments are capable of penetrating neuronal cell membrane as well as the blood-brain-barrier (see FIGS. 6 and 7). Other preferred administration routes are subcutaneous, intrathecal, intracerebroventricular, intranasal, or transdermal administration.

Figure 13:
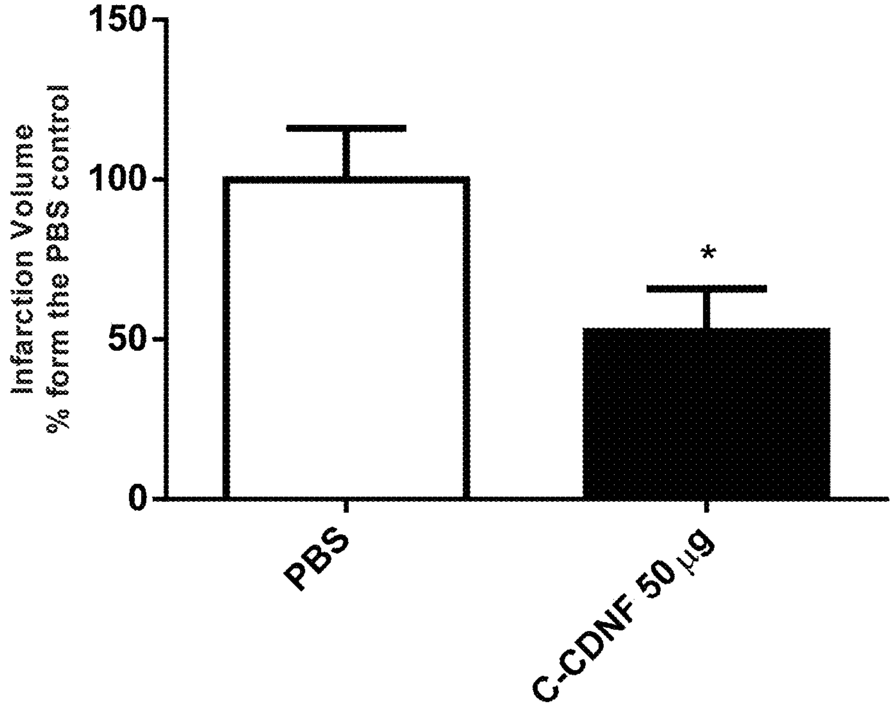
FIG. 13. Subcutaneously injected C-CDNF decreases infarction volume in a rat model of cerebral ischemia. C-CDNF (50 μg) was administered 30-50 minutes before distal middle cerebral artery occlusion and right after reperfusion in a volume of 100 μl. C-CDNF treatment decreases the infarction volume when measured from the rostral part of the cerebral cortex (Student's t-test $p<0.05$). The C-CDNF treated rats had about 50% smaller lesions than the vehicle treated rats. PBS was used as control. * indicates $P<0.05$. The values are expressed as mean±SEM as percentage from the PBS, n=8-9. Systematically administered C-CDNF does not affect blood pressure and heart rate. Alterations in blood pressure and heart rate are well-known to cause alterations in lesion volume, and thus this data suggest that C-CDNF has direct neuroprotective effect.

In FIG. 13, the effect of a subcutaneous injection of C-CDNF protein is shown in rats having an induced cerebral stroke.

Suitable examples of sustained-release preparations include semipermeable matrices of solid hydrophobic polymers containing the fragment, which matrices are in the form of shaped articles, e.g., films, or microcapsules. Examples of sustained-release matrices include polyesters, hydrogels as described by Langer et al., J. Biomed. Mater.

Res., 15:167-277 (1981) and Langer, Chem. Tech., 12:98-105 (1982) or polyvinylalcohol, polylactides (U.S. Pat. No. 3,773,919, EP 58,481), or non-degradable ethylene-vinyl acetate (Langer et al., supra).

Gene therapy vectors can be delivered to a subject using corresponding administration modes as defined above for the peptide fragment, preferably by, for example, intravenous injection, or by intraperitoneal, subcutaneous, intrathecal, or intracerebroventricular administration. The pharmaceutical preparation of a gene therapy vector can include an acceptable diluent, or can comprise a slow release matrix in which the gene delivery vehicle is embedded.

Figure 14:
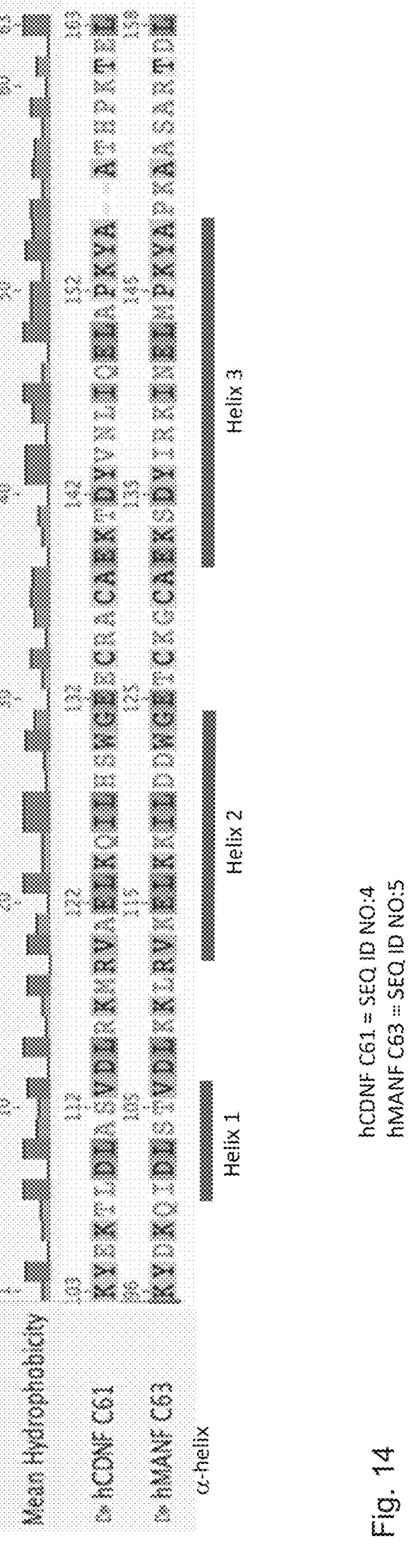
FIG. 14. Sequence alignment and comparison of C-CDNF and C-MANF. The C-terminal structure of both neurotrophic factors comprises three alpha-helix motifs (helix 1, 2 and 3).

The sequence alignment of FIG. 14 shows the high sequence identity of C-terminal CDNF and MANF peptides. Accordingly, the present inventors extrapolate from the results presented herein that also in the C-terminal MANF fragment the amino acid sequence motifs important for cell membrane penetration and for protective effect on neuronal cells are similarly located in the sequence. The present invention is thus directed to a C-terminal MANF fragment consisting of at least 50 consecutive amino acid residues of the sequence as set forth in SEQ ID NO: 2:

```
ICEKLKKKDS QICELKYDKQ IDLSTVDLKK LRVKELKKIL

DDWGETCKGC AEKSDYIRKI NELMPKYAPK AASARTDL
```

or a sequence which has at least 90% homology or sequence identity to the sequence of SEQ ID NO: 2 for use in the treatment of a degenerative disease or disorder including central nervous system (CNS) diseases, wherein said fragment is administered by intravenous or peripheral administration, intraperitoneal, subcutaneous, intranasal, transdermal, intramuscular, intraocular, or intraarterial administration.

Based on the results shown in FIG. 10, the present invention is further directed to a C-terminal MANF fragment consisting of at least 50 consecutive amino acid residues of the sequence as set forth in SEQ ID NO:2:

```
ICEKLKKKDS QICELKYDKQ IDLSTVDLKK LRVKELKKIL

DDWGETCKGC AEKSDYIRKI NELMPKYAPK AASARTDL
```

or a sequence which is at least 90% homologous to the sequence of SEQ ID NO:2 for use in the treatment of type 1 or type 2 diabetes.

For all above-mentioned embodiments, said sequence which is at least 90% homologous to the sequence of SEQ ID NO:2 preferably comprises sequence CXXC in positions 47-50 of SEQ ID NO:2, wherein X is any amino acid.

More preferably, said sequence which is at least 90% homologous to the sequence of SEQ ID NO: 2 consists of at least 50 consecutive amino acid residues of the sequence of SEQ ID NO: 6:

```
QICELKYDKQ IDLSTVDLKK LRVKELKKIL DDWGETCXXC

AEKSDYIRKI NELMPKYAPK AASARTDL
```

wherein X is any amino acid.

Most preferably, said MANF fragment has the sequence of SEQ ID NO:5:

```
KYDKQ IDLSTVDLKK LRVKELKKIL DDWGETCKGC AEKSDYIRKI

NELMPKYAPK AASARTDL
```

or a sequence which is at least 90% homologous to the sequence of SEQ ID NO:5

In an embodiment, the C-terminal MANF fragment does not contain its natural C-terminal amino acids, i.e. the ER retention signal. Accordingly, in a preferred embodiment the fragment lacks the ER retention signal RTDL (SEQ ID NO:14) corresponding to positions 75-78 of SEQ ID NO:2.

The C-terminal MANF fragment can be modified in the same way as is discussed above for the C-terminal CDNF fragment.

The present invention is further directed to a pharmaceutical composition comprising the C-terminal MANF fragment and at least one of the following: physiologically acceptable carrier, buffer, excipient and stabilizer for use in the treatment of central nervous system (CNS) disease, type 1 or type 2 diabetes or a retinal disorder. Said pharmaceutical composition comprising the C-terminal MANF fragment is preferably administered to a patient peripherally and is thus preferably suitable for peripheral administration.

The present specification is also directed to methods for treatment of a degenerative disease or disorder including a central nervous system (CNS) disease, type I or type II diabetes or a retinal disorder, wherein a pharmaceutically effective amount of the C-terminal CDNF fragment or the C-terminal MANF fragment as defined herein is administered to a patient.

Preferably, said fragment is administered peripherally.

The present specification is also directed to a use of the C-terminal CDNF fragment or the C-terminal MANF fragment as defined herein for the manufacture of a medicament for the treatment of a degenerative disease or disorder including a central nervous system (CNS) disease, type I or type II diabetes or a retinal disorder.

The present invention also provides an isolated polynucleotide comprising a nucleotide sequence encoding the C-CDNF fragment having the sequence of SEQ ID NO:4:

```
KYEKTLDLAS VDLRKMRVAE LKQILHSWGE ECRACAEKTD

YVNLIQELAP KYAATHPKTE L
```

or a sequence which has at least 90% homology or sequence identity to the sequence of SEQ ID NO: 4.

The invention further provides an expression vector encoding said isolated polynucleotide and a host cell transformed with said vector. The selection of recombinant vectors suitable for expressing said isolated polynucleotide, methods for inserting nucleic acid sequences for expressing the C-CDNF fragment into the vector, and methods of delivering the recombinant vector to the cells of interest are within the skill in the art. See, for example Tuschl, T. (2002), Nat. Biotechnol, 20:446-448.

The publications and other materials used herein to illuminate the background of the invention, and in particular, to provide additional details with respect to its practice, are incorporated herein by reference. The present invention is further described in the following examples, which are not intended to limit the scope of the invention.

EXPERIMENTAL SECTION

Studies with Superior Cervical Ganglia Cells

For the cultures of sympathetic neurons (Hellman et al., 2011; Hamner et al., 2001; Lindholm et al., 2002; Sun et al., 2001; Aalto et al., 2007) the superior cervical ganglia from the postnatal day (P) 0-3 mice were digested with collagenase (2.5 mg/ml; Worthington), dispase (5 mg/ml; Roche Molecular Biochemicals), and trypsin (10 mg/ml; Worthington) for 45 min at 37° C. and dissociated mechanically with a siliconized glass Pasteur pipette. Non-neuronal cells were removed by extensive preplating. Almost pure neurons were cultured in polyornithine/laminin (Sigma)-coated 35-mm plastic dishes in the small-size standard microislands in the Neurobasal medium and B27 supplement (Invitrogen/Gibco) in the presence of 30 ng/ml mouse nerve growth factor (NGF) (Promega) for 5-6 days. NGF was deprived by extensive washing and addition of the function-blocking anti-NGF antibodies (Roche). The neurons were pressure-microinjected with special neuronal microinjection equipment (Hellman et al., 2011; Hamner et al., 2001; Lindholm et al., 2002; Sun et al., 2001; Yu et al., 2003) (Sun et al., 2001; Sun et al., 2003). For the survival assay, all neurons on the microislands were counted in the beginning (initial number) and the end (three days) of the experiment and expressed as % of initial.

Microinjection of the sympathetic neurons was performed as described earlier (Yu, L. Y., Jokitalo, E., Sun, Y. F., Mehlen, P., Lindholm, D., Saarma, M., and Arumäe, U. (2003) *J. Cell Biol.* 163, 987-997). Plasmids for CDNF have been described earlier. Briefly, newborn mouse SCG neurons were grown with NGF (Promega) for 5-6 days then the nuclei were microinjected with the expression plasmids for full-length (FL)-CDNF and C-CDNF together with a reporter plasmid for enhanced green fluorescent protein (EGFP), using vector concentration of 10 ng/ul in each experiment. Similar results were achieved with plasmid concentrations of 50 ng/ul. For protein microinjection, recombinant full length (FL)-CDNF, C-CDNF proteins in PBS at 200 ng/ul were microinjected directly into the cytoplasm together with fluorescent reporter Dextran Texas Red (MW 70000 Da) (Invitrogen, Molecular Probes) that facilitates identification of the successfully injected neurons. Next day tunicamycin (2 μM) was added, and after 3 days the living fluorescent neurons were counted. Living fluorescent (EGFP-expressing or Dextran Texas Red-containing) neurons were "blindly" counted three days later and expressed as percent of initial living fluorescent neurons counted 2-3 hours after microinjection. The experiments with plasmids were repeated on independent cultures 5 times for plasmid experiment, whereas four independent protein injection experiments were performed. On average, 50-80 neurons were successfully injected per experimental group. The results were expressed as the mean±the SEM. Data of each experimental group was compared with control plasmid PCR3.1 (vector) or PBS (in the protein injection experiments) by one-way ANOVA and post hoc Dunnett's t test. The null hypothesis was rejected at $p<0.05$.

CDNF Expression Plasmids

Constructs coding for full-length (FL) or carboxy-terminal (C) domains were inserted to pCR3.1 vector (Invitrogen) either by TOPO/TA cloning system (Invitrogen) or by using restriction endonucleases. Full-length CDNF in pCR3.1 vector are 537 bp (179 amino acids) and 561 bp (187 amino acids) amino acids long, respectively and have in their N-termini signal sequence for ER targeting. C-CDNF is 186 bp long, corresponding to amino acids 127-187 in FL-CDNF.

| | |
|---|---|
| E511 | Human CDNF in pCR3.1/Bidirectional TOPO TA. Full-length cDNA with stop codon (No tags). Ampicillin selection. DH5α. Verified by sequencing. |
| E811 | pCR3.1 hCDNF C- human CDNF C terminal sequence with signal sequence. Cloned by PCR and Invitrogen TA cloning system. Insert size 207bp. Transformed into DH5a cells. Amp selection. Verified by sequencing. |

Plasmids Expressing Proteins and Peptide Fragments

Human recombinant CDNF (full length pre-CDNF consisting of the 187 amino acids, with 26 amino acids long signal sequence and 161 amino acids long mature CDNF sequence), human N-CDNF (consisting of human CDNF signal sequence of 26 amino acids and the part of the mature CDNF from amino acid 1-amino acid 100) and human C-CDNF (consisting of 26 amino acids long CDNF signal sequence fused with the C-terminal domain of mature CDNF starting from amino acid 101 spanning to amino acid 161).

Human recombinant MANF (full length pre-MANF consisting of the 179 amino acids, with 21 amino acids long signal sequence and 158 amino acids long mature MANF sequence), human N-MANF (consisting of human MANF signal sequence of 21 amino acids and the part of the mature MANF from amino acid 1-amino acid 95) and human C-MANF (consisting of 21 amino acids long CDNF signal sequence fused with the C-terminal domain of mature MANF starting from amino acid 96 spanning to amino acid 158).

Codon optimized cDNA synthesis for hMANF and hCDNF and their domains was ordered from Genewiz and respective pQMCF expression vectors were constructed. N-CDNF, C-CDNF, N-MANF and C-MANF constructs had Histidine tag at the C-terminus. cDNA-s were verified by sequencing in final vectors. hMANF and hCDNF proteins were produced by CHO-derived suspension cell line CHOEBNALT85, chemically defined serum-free media was used for culturing of the cells.

CHOEBNALT85 cells were transfected with 1 μg of the expression plasmids. 48 h after the transfection 700 μg/ml of G418 was added to select plasmid containing cell population. The expression and secretion of the proteins were analyzed 48 h after transfection in reduced conditions in cell lysates and in supernatants.

hMANF and hCDNF proteins were purified by two-step ion-exchange chromatography and gelfiltrated into PBS, pH 7.4. Based on the SDS-PAGE and Western blotting analysis with CDNF and MANF antibodies (MANF 4E12-HRP and CDNF-7D6-HRP, Icosagen Tartu, Estonia) the used proteins were more than 99% pure.

CDNF and MANF C- and N-terminal domains were purified on Ni-affinity column and the proteins were also analysed buy SDS-PAGE and Western blotting using mouse monoclonal antibody to His tag (Cat No. A00186; GeneScript). The produced proteins had the following sequence:

```
Mature human CDNF:
                                          (SEQ ID NO: 7)
QEAGGRPGADCEVCKEFLNRFYKSLIDRGVNFSLDTIEKELISFCLDTKG

KENRLCYYLGATKDAATKILSEVTRPMSVHMPAMKICEKLKKLDSQICEL
```

-continued

```
KYEKTLDLASVDLRKMRVAELKQILHSWGEECRACAEKTDYVNLIQELAP

KYAATHPKTEL

Human N-CDNF:
                                        (SEQ ID NO: 8)
QEAGGRPGADCEVCKEFLNRFYKSLIDRGVNFSLDTIEKELISFCLDTKG

KENRLCYYLGATKDAATKILSEVTRPMSVHMPAMKICEKLKKLDSQICEL

Human C-CDNF:
                                        (SEQ ID NO: 4)
KYEKTLDLASVDLRKMRVAELKQILHSWGEECRACAEKTDYVNLIQELAP

KYAATHPKTEL

Mature human MANF:
                                        (SEQ ID NO:9)
LRPGDCEVCISYLGRFYQDLKDRDVTFSPATIENELIKFCREARGKENRL

CYYIGATDDAATKIINEVSKPLAHHIPVEKICEKLKKKDSQICELKYDKQ

IDLSTVDLKKLRVKELKKILDDWGETCKGCAEKSDYIRKINELMPKYAPK

AASARTDL

Human N-MANF
                                       (SEQ ID NO: 10)
LRPGDCEVCISYLGRFYQDLKDRDVTFSPATIENELIKFCREARGKENRL

CYYIGATDDAATKIINEVSKPLAHHIPVEKICEKLKKKDSQICEL

Human C-MANF
                                        (SEQ ID NO: 5)
KYDKQIDLSTVDLKKLRVKELKKILDDWGETCKGCAEKSDYIRKINELMP

KYAPKAASARTDL
```

Studies with Dopamine Neurons

To study the dopamine neurons (Yu et al., 2008; Yu and Arumae, 2008), the midbrain floors were dissected from the ventral mesencephali of 13.5-d-old NMRI strain mouse embryos. Tissues were incubated with 0.5% trypsin (ICN Biomedical), then mechanically dissociated using a large fire-polished Pasteur pipette. The neurons were grown on the poly-L-ornithine-coated (Sigma) 96-well culture plates in DMEM/F12 medium (Invitrogen) containing N2 supplement (Invitrogen) in the presence or absence of GDNF (100 ng/ml) or with CDNF, MANF, C-CDNF and C-MANF polypeptides at different concentrations for five days. Same amount of the neurons were plated to each well at the beginning of the experiments. The cultures without added neurotrophic factors served as the negative control. As the midbrain cultures contain several neuronal types, the cultures were fixed and immunostained with the antibodies to tyrosine hydroxylase (TH) (Millipore), a specific marker for the dopaminergic neurons. Images of each well were scanned by CellInsight™ and immunopositive neurons were counted by CellProfiler and CellProfiler analyst software. Data are expressed as a percentage of GDNF-maintained TH-positive neurons. All experiments were repeated at least three times on the independent cultures. The results were expressed as the mean the SEM and were tested for the significance by either one-way ANOVA and Tukey's post hoc test or by two-tailed Student's t-test. The null hypothesis was rejected at $P \leq 0.05$.

Iodination of CDNF, C-CDNF and C-MANF

CDNF, C-CDNF and C-MANF were iodinated with $^{125}$I-Na using the lactoperoxidase method. The protein in question was dissolved in 30 μl of 0.25 M phosphate buffer, pH 7.5, and mixed with $^{125}$I-Na (1 mCi/2.8 μl; 1 mCi=37 mBq; GE Healthcare). The reaction was started by adding lactoperoxidase 10 μl of 50 μg/ml and 0.05% $H_2O_2$. The mixture was incubated at room temperature for 20 min and the reaction was stopped by adding 3 volumes of 0.1 M phosphate buffer, pH 7.5, containing 0.1 M NaI, 0.42 M NaCl, and then 25 μl of 2.5% BSA was added. Free iodine and iodinated protein were separated by gel filtration on Sephadex G-25 columns (PM10; GE Healthcare). For column equilibrium and elution, 0.1 M phosphate buffer, pH 7.5, with 1% BSA was used. The iodinated growth factors were sometimes concentrated by using YM-10 Centricon columns (Millipore). The specific activity of $^{125}$I-labeled CDNF, C-CDNF, N-CDNF, C-MANF and N-MANF was measured on the Wizard 3 1480 Automatic Gamma Counter (Perkin Elmer, Wallac) and was about 108 cpm/μg protein. The labelled protein were kept at 4° C. and used within 3 weeks after labelling.

Internalization Experiment on E13.5 Dopaminergic Neurons

Mouse E13.5 dopamine neurons grown on the 24 well plate in culture were incubated with 30,000 cpm of iodinated CDNF or C-CDNF per well at 37° C. 2 hr. The cells were transferred to ice and washed once with 0.5 ml of the ice cold media. Then cells were transferred to Eppendorf tubes and washed at 4° C. once with 0.2M acetic acid, 0.5M NaCl, pH 2.8. After centrifugation at 1000 g for 10 min cells were dissolved in 0.5 ml of 0.5 N NaOH and counted on the Wizard 3 1480 Automatic Gamma Counter (Perkin Elmer, Wallac).

Blood-Brain Barrier Penetration Study in Rats $^{125}$I-CDNF, $^{125}$I C-CDNF or $^{125}$I C-MANF (all proteins at 106 cpm in 10 μl) were injected subcutaneously to adult male Wistar rats. Animals were perfused with PBS 2 hours later. Radioactivity was analyzed in different brain regions by gamma counter. Data are shown as mean±SEM. The differences between groups were analyzed ANOVA followed by Tukey-Kramers post hoc test.

Internalization Experiment on PC6.3 Cells

Rat PC6.3 pheochromocytoma cells were grown on the 24 well plate in DMEM culture with 10% FCS and 5% horse serum. The cells were washed with PBS and were incubated with 30,000 cpm of iodinated CDNF, C-CDNF or C-MANF per well at 37° C. 90 min. The cells were put on ice, washed once with 0.5 ml of the ice cold media. Then cells were transferred to Eppendorf tubes and washed once with 0.2M acetic acid, 0.5M NaCl, pH 2.8. After centrifugation at 1000 g for 10 min cells were dissolved in 0.5 ml of 0.5 N NaOH and counted in Wizard 3 1480 Automatic Gamma Counter (Perkin Elmer, Wallac).

Neurorestoration Study in 6-OHDA Model of PD in Rats

In neurorestoration model of PD, rats were lesioned with 6-OHDA as described before (Voutilainen et al., 2009; Voutilainen et al., 2011, Penttinen et al., 2016). Briefly, rats received under isoflurane anesthesia unilateral stereotaxic injections of 3×2 μg 6-OHDA (in 10 degree angle) into the left striatum (coordinates relative to bregma and dura A/P+1.6; L/M−2.8; D/V−6, A/P 0.0: L/M−4.1; D/V−5.5 and A/P−1.2; L/M: −4.5; D/V−5.5). Two weeks later, rats were divided to groups based on their amphetamine-induced rotation results (size of the lesion). Thereafter CDNF (10 μg), C-CDNF (equimolar to CDNF 10 μg) and N-CDNF (equimolar to CDNF 10 μg) were injected intrastriatally to rats using to the same coordinates as the 6-OHDA. In the reference experiment after division of rats into groups, osmotic minipumps were inserted subcutaneously and cannula was placed into lesioned striatum. The minipump delivered MANF4 (i.e. MANF peptide CKGC, SEQ ID NO:12, see WO2013034805), GDNF or vehicle solution into striatum for two weeks after which the minipump and cannula were removed. Inside neurons 6-OHDA has two ways of action that act synergistically: 1) it accumulates in the cytosol and forms free radicals causing oxidative stress; 2) it is a potent inhibitor of the mitochondrial respiratory chain complexes I and IV. Noradrenergic neurons were protected by using a NAT-inhibitor desipramine (15 mg/kg, i.p., 30 mins before 6-OHDA-injection). The size of the unilateral lesion and the effect of the treatments were measured with amphetamine induced rotational behavior 2, 4, 6 and 8 weeks after the lesion in the experiment involving CDNF, C-CDNF, N-CDNF and PBS treated rats, and at 1,4,8,10 and 12 weeks in the reference experiment with involving MANF4 and GDNF. The number of amphetamine-induced (2.5 mg/kg, i.p.) full (360°) ipsi- and contralateral turns were recorded for 120 mins after a 30 min habituation period. The results are expressed as net ipsilateral turns to the lesion side Exclusion criterion was Mean (net rotations)±2×STDEV.

Tyrosine Hydroxylase (TH)—Immunohistochemistry

Perfusion and tissue processing. Immediately after neurorestoration studies, the rats were anesthetized with an overdose of sodium pentobarbital (90 mg/kg, i.p.; Orion Pharma) and perfused intracardially with PBS followed by 4% paraformaldehyde in a 0.1 M sodium phosphate buffer, pH 7.4. The brains were removed, postfixed for 4 h and stored in sodium phosphate buffer containing 20% sucrose at 4° C. Serial coronal frozen sections of 40 μm depth were cut on a sliding microtome. Immunohistochemistry was performed as described elsewhere (Voutilainen et al., 2009), The perfused brains were postfixed overnight in paraformaldehyde at 4° C. and stored in 20% sucrose. The brains were cut into 40-μm-thick sections in series of six. Free-floating sections were washed with phosphate-buffered saline (PBS), and the endogenous peroxidase activity was quenched with 0.3% hydrogen peroxide (Sigma Aldrich). To block the nonspecific binding of antibodies, the sections were incubated for 1 hr in blocking buffer (4% bovine serum albumin and 0.1% Triton X-100 in 1×PBS). The sections were incubated overnight in mouse monoclonal anti-tyrosine hydroxylase (TH) antibody (1:2,000; catalog No. MAB318; RRID:AB_2201528; Millipore, Billerica, MA) in blocking buffer at 4° C., followed by incubation in biotinylated secondary antibody (1:200; anti-rat or anti-mouse; Vector, Burlingame, CA). The staining was augmented with avidin-biotin-enzyme complex (ABC kit; Vector), and the signal was visualized with 3',3'-diaminobenzidine as a chromogen.

TH—Positive Cell Count from Substantia Nigra

TH-positive cells in the substantia nigra pars compacta (SNpc) were analyzed from six sections spanning the SNpc, from approximately A/P−4.5 to −6.0 relative to bregma. Cells were counted with a Matlab (RRID:nlx_153890; MathWorks, Natick, MA) algorithm from the images obtained with the 3DHistech scanner. The resolution of the scanner was 0.24 μm/pixel with a ×20 NA 0.8 objective.

Optical Density Analyses of TH-Positive Neurites in Striatum

The optical densities of the TH-positive neurites in the striatum were determined from three striatal sections, from approximately A/P+2.2, +0.84, and −0.12 relative to bregma from each rat. To decrease background signal, the sections were scanned with an automated scanner (3DHistech, Budapest, Hungary, with scanning service provided by the Institute of Biotechnology, University of Helsinki), and the images were converted to 16-bit gray scale. Because the corpus callosum was devoid of TH signal, it was used as a measure of nonspecific background staining. The integrated densities divided by area from the obtained images were analyzed in ImageJ (NIH). Data are presented as percentage of the intact side.

Beta Cell Proliferation Assay

Islets from female, virgin 8 weeks old C57b16Rcc mice were isolated. Islets were recovered o/n in growth medium and the next day equal numbers of islets/well (70/well) were treated for 5 days with placental lactogen (PL 500 ng/ml), C-MANF, or MANF. Half of the medium was changed daily to fresh medium with growth factors. Edu, a nucleoside analog alternatively to BrdU (Click-iT®Edu proliferation kit, Invitrogen) was added 48 hrs prior to islet harvesting.

Islets were broken with trypsin and centrifuged onto glass slides in cytocentrifuge. Cells were fixed after cytospins and proliferating cells stained with Click-iT AlexaFluor azide color reagent, followed by insulin staining (guinea-pig 1:200, Abcam, Cambridge, UK) o/n at +4° C. to detect beta cells. Cells were washed and stained with secondary antibodies conjugated with Alexa Fluor® 488 (1:400, Molecular Probes, Life Technologies, CA, USA). Slides were mounted with Vectashield mounting medium containing DAPI (Vector Laboratories, Inc., Burlingame, CA, USA). Twelve images (10× magnification) were acquired with Fluorescence Zeiss AxioImager M2 482 epifluorescence microscope equipped with 40×/Plan-Apochromat/0.95 Corr M27 and 63×/Plan-Apochromat/1.40 Oil/M27 and 483 AxioCam HRm camera using AxioVision4 software and analysed by Image Pro Plus software (Media Cybernetics, Bethesda, MD, USA) to quantify number of DAPI-positive nuclei. The relative numbers of proliferating beta cells were quantified and compared to wells of three to five repeats/treatment.

The Mouse Model of ALS

Transgenic SOD1 G93A mice served as a transgenic mouse model for ALS in this study. Transgenic mice containing various human SOD1 mutations develop progressive neurodegeneration and motoneuron (MN) death, providing an animal model that has been commonly used for preclinical trials and that has greatly contributed to the understanding of FALS pathogenesis (Gurney et al., 1994). Transgenic SOD1 mice exhibit the ALS-like clinical features that are transmitted in an autosomal dominant fashion. In these mice hind limb weakness and tremulous movement appear as initial symptoms at 8-10 week of age, followed by major symptoms such as progressive motor paralysis and neurogenic amyotrophy (Shibata 2001). These mice subsequently show disability of gait, eating and drinking and die within some weeks, usually at 14-16 week of age. The transgenic mice carrying the human SOD1 with the glycine93 to alanine mutated were originally obtained from The Jackson Laboratory (http://www.jax.org), Bar Harbor, ME; Strain B6SJL-TgN (SOD1-G93A) 1Gur). Transgenic expression was analyzed by DNA tail tests and PCR, using specific oligonucleotides and conditions as done previously by others (see homepage Jackson Lab). In all the experiments the wild-type B6SJL-TgN (SOD1) 2Gur were included as controls.

Experimental Set-Ups in ALS Mice

In the single administration experiment, mice at around 13 weeks of age received a single intracerebroventricular injection of PBS or C-CDNF (3.75 μg that is equimolar to full-length CDNF 10 μg diluted in PBS) under isofluorane anesthesia. Mice were then evaluated for signs of disease and body weight changes twice a week. Evaluation was completed by a battery of behavioral tests designed to assess motor activity in the mice; the battery comprises tests e.g. rotarod.

In the chronic infusion experiment, 12-week-old SOD1 mice were inserted a brain infusion cannula (connected via catheter-tubing to an Alzet osmotic minipump) to the right lateral ventricle under isoflurane anesthesia. C-CDNF (1.5 μg/24 h) was infused for 28 days. Motor behavior was evaluated with rotarod. Mice were evaluated for clinical signs and body weight changes.

Clinical Scoring of ALS Mice

Clinical scoring for SOD1 mice was done using instructions from Jackson laboratory. The mice were carefully examined 2 times a week after they were 12 weeks old. Animals were scored by lifting them gently by the base of their tails and observing them for tremors, stiffness and their ability to extend their limbs. The clinical scoring is on a scale of 1 to 5, based on ALSTDI (ALS therapy Development Institute) hind limb neurological scoring system.

Rotarod

In rotarod, mice were put to a rotating rod (accelerating speed 4-40 rpm/minute), (Ugo Basile, Italy). Cut off time was 4 minutes. Rotarod test was done 2 times a week after the mice were 12 weeks old.

Distal Occlusion of the Middle Cerebral Artery as a Model of Cerebral Stroke

Male Sprague Dawley rats (weight 230-270 g, Envigo, Netherlands) were used for the experiments which were conducted according to the 3R principles of EU directive 2010/63/EU on the care and use of experimental animals, local laws and regulations, and were approved by the national Animal Experiment Board of Finland All experiments were performed in a blinded manner and the rats were assigned to different treatment groups randomly. Rats were anesthetized with chloral hydrate (0.4 g/kg, i.p). A cortical stroke was induced by occluding the distal middle cerebral artery (dMCA) together with a bilateral common carotid artery (CCA) occlusion for 60 min as described previously (Chen, et al., 1986). Briefly, the bilateral CCAs were identified and isolated through a ventral midline cervical incision. Rats were placed in stereotaxic apparatus and a craniotomy was made in the right hemisphere. The right (MCA) was ligated with a 10-0 suture and bilateral common carotids (CCA) were ligated with non-traumatic arterial clamps for 60 minutes. After sixty minutes of ischemia, the suture around the MCA and arterial clips on CCAs were removed to introduce a reperfusional injury. After recovery from anesthesia, the rats were returned to their home cage. Body temperatures during and after surgery were maintained at 37° C.

To test the neuroprotective effect of subcutaneous C-CDNF, 50 μg of C-CDNF was given 30-50 min before dMCA occlusion and immediately after reperfusion in volume of 100 μl s.c. Phosphate-buffered saline (PBS) was used as vehicle control. The rats were euthanized 2 days after dMCAo to measure the infarction volume by 2% 2,3,5-triphenyltetrazolium chloride (TTC; Sigma Aldrich, St. Louis, MO) staining. Rats were decapitated and the brains were removed and sliced into 2.0-mm-thick sections using an acrylic rat brain block. The brain slices were incubated in a 2% TTC solution (Sigma, St. Louis, MO, USA) for 15 min at room temperature and then transferred into a 4% paraformaldehyde solution for fixation. The area of infarction in each slice was measured with a digital scanner and ImageJ software. The volume of infarction in each animal was obtained from the product of average slice thickness (2 mm) and sum of infarction areas in rostral brain slices examined. Student's t-test was used for statistical analysis.

Effect of C-CDNF Injected s.c. In Healthy Animals

Figure 15:
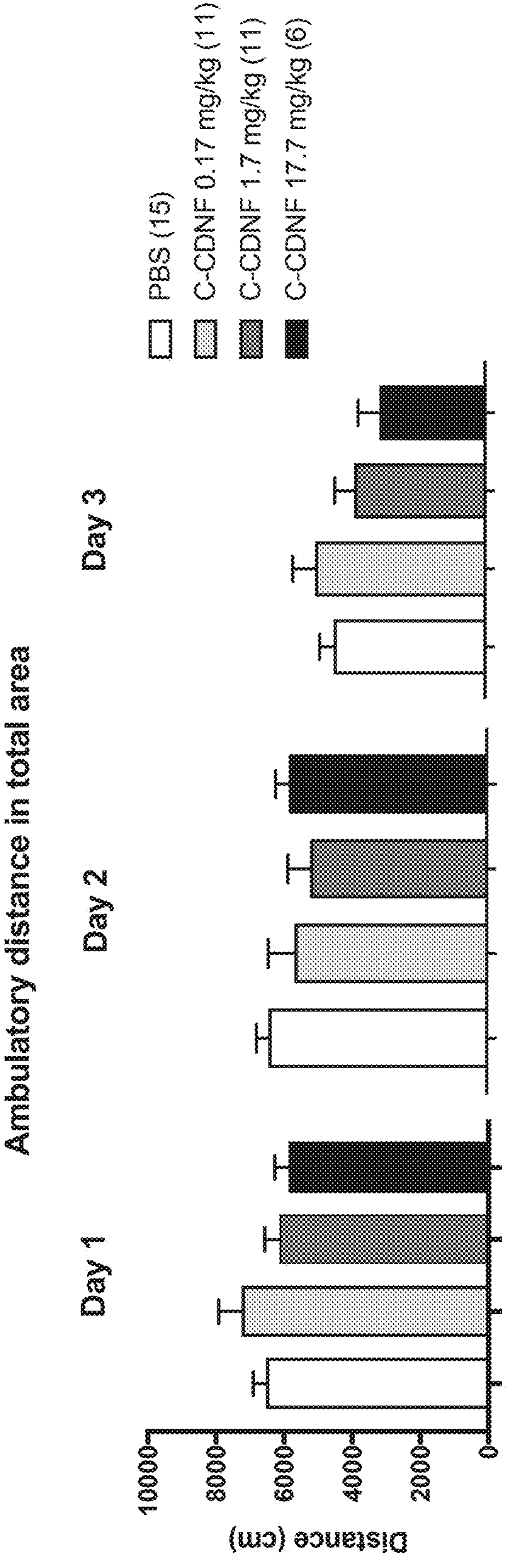
FIG. 15. Effect of C-CDNF injected subcutaneously in wild type mice. Results from open field experiments. Subcutaneous administration of different doses of C-CDNF does not affect locomotor activity.

Wild type mice received 2 injections of C-CDNF (0.17 mg/kg, 1.77 or 17.7 mg/kg) per week for 3 weeks. Locomotor activity of mice was measured for 60 minutes in an open field test once a week right after the subcutaneous C-CDNF injection. No weight changes were seen after repeated C-CDNF s.c injections. No statistical difference in behavioral patterns was detected between the control group and the group receiving a dose of C-CDNF. Results are shown in FIG. 15.

Effect of C-CDNF in Huntington's Disease Rat Model

Adult Wistar rats received a single, unilateral intrastriatal injection of quinolinic acid (QA) 225 nmol into coordinates: A/P+0,7; L/M+2,8; D/V−6,0. Quinolinic acid is a toxin that induces striatal neuron death by an excitotoxic process. 2 weeks later rats received single intrastriatal injections of PBS, CDNF (10 micrograms), C-CDNF (amount equivalent to equimolar amount of CDNF) to the same coordinates. Rats were randomized to groups before the treatments started. Rotarod and grip strength tests were done weekly.

Figure 16A:
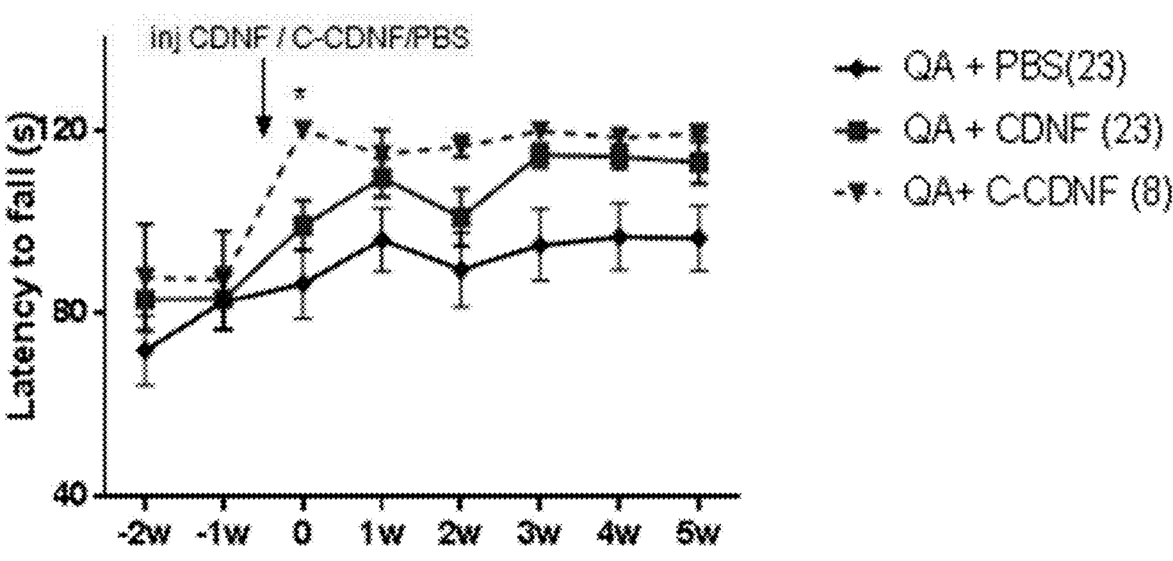
FIGS. 16A-B. Effect of C-CDNF in a Huntington's disease model.
Figure 16B:
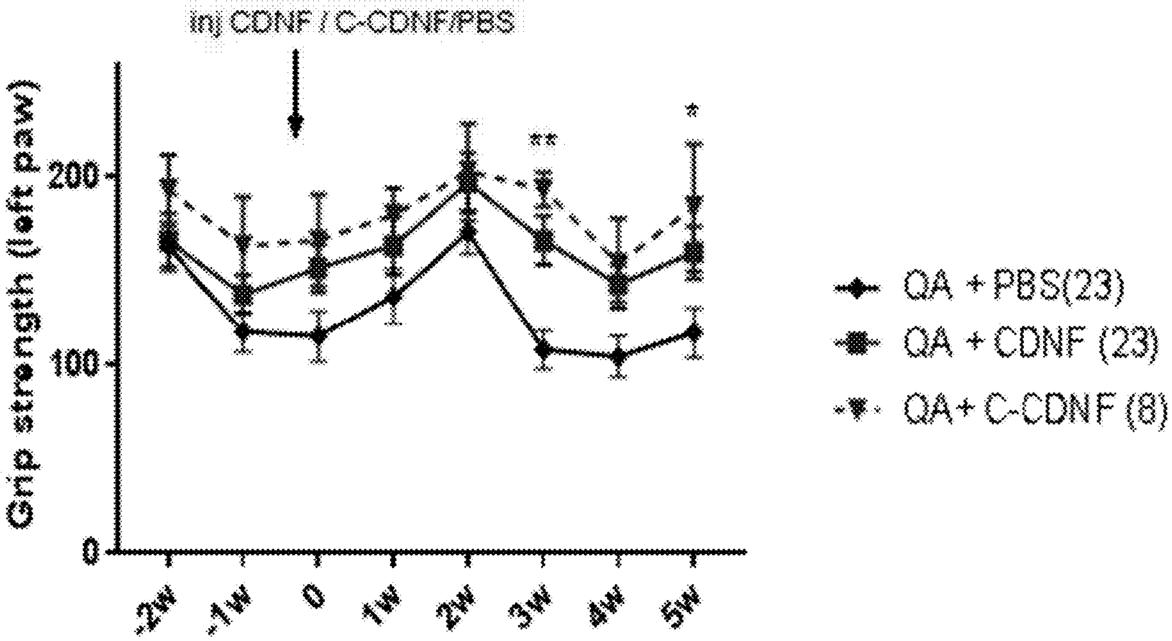

Only C-CDNF and not CDNF improved motor behavior statistically significantly after quinolinic acid lesioning in rotarod test and in the grip strength test C-CDNF resulted in significantly improved performance at 3 and 5 week time points. Results are shown in FIGS. 16A-B.

REFERENCES

Aalto, A. P., L. P. Sarin, A. A. van Dijk, M. Saarma, M. M. Poranen, U. Arumae, and D. H. Bamford. 2007. Large-scale production of dsRNA and siRNA pools for RNA interference utilizing bacteriophage phi6 RNA-dependent RNA polymerase. *RNA.* 13:422-429.

Airavaara, M., H. Shen, C. C. Kuo, J. Peranen, M. Saarma, B. Hoffer, and Y. Wang. 2009. Mesencephalic astrocyte-derived neurotrophic factor reduces ischemic brain injury and promotes behavioral recovery in rats. *J. Comp. Neurol.* 515 (1): 116-124.

Airavaara M, Harvey B K, Voutilainen M H, Shen H, Chou J, Lindholm P, Lindahl M, Tuominen R K, Saarma M, Hoffer B, and Wang Y. CDNF protects the nigrostriatal dopamine system and promotes recovery after MPTP treatment in mice. Cell Transplant. 2012; 21 (6): 1213-23. doi: 10.3727/096368911X600948.

Bai M, Vozdek R, Hnízda A, Jiang C, Wang B, Kuchar L, Li T, Zhang Y, Wood C, Feng L, Dang Y, and Ma D K. Conserved roles of *C. elegans* and human MANFs in sulfatide binding and cytoprotection. *Nat Commun.* 2018 Mar. 1; 9 (1): 897. doi: 10.1038/s41467-018-03355-0.

Bode & Löwik, Constrained cell penetrating peptides. *Drug Discovery Today*: Technologies; 2017, Vol. 26, pages 33-42

Borrelli A, Tornesello A L, Tornesello M L, Bonagura F M. Cell Penetrating Peptides as Molecular Carriers for Anti-Cancer Agents. Molecules. 2018 Jan. 31; 23 (2). pii: E295. doi: 10.3390/molecules23020295.

Chen S T, Hsu C Y, Hogan E L, Maricq H, Balentine J D. A model of focal ischemic stroke in the rat: reproducible extensive cortical infarction. Stroke. 1986; 17 (4): 738-743.

Dornburg R (1995), *Gene Therap.* 2:301-310.

Gurney, M E., Cutting, F B., Zhai, P., Doble, A., Taylor, C P., Andrus, P K. and Hall, E D. 1996 Benefit of vitamin E, riluzole, and gabapentin in a transgenic model of familial amyotrophic lateral sclerosis. Ann Neurol 39 (2) 147-57

Hamner, S., U. Arumae, Y. Li-Ying, Y. F. Sun, M. Saarma, and D. Lindholm. 2001. Functional characterization of two splice variants of rat bad and their interaction with Bcl-w in sympathetic neurons. *Mol. Cell. Neurosci.* 17:97-106.

Hellman, M., U. Arumae, L. Y. Yu, P. Lindholm, J. Peranen, M. Saarma, and P. Permi. 2011. Mesencephalic astrocyte-derived neurotrophic factor (MANF) has a unique mechanism to rescue apoptotic neurons. *J. Biol. Chem.* 286:2675-2680.

Kalafatovic & Giralt, Cell-Penetrating Peptides: Design Strategies beyond Primary Structure and Amphipathicity. Molecules. 2017 Nov. 8; 22 (11). pii: E1929. doi: 10.3390/molecules22111929.

Mie Kristensen, Ditlev Birch and Hanne Mørck Nielsen. Applications and Challenges for Use of Cell-Penetrating Peptides as Delivery Vectors for Peptide and Protein Cargos. Int. J. Mol. Sci. 2016, 17, 185; doi: 10.3390/ijms17020185

Lindahl M, Saarma M, Lindholm P, M. 2017 Unconventional neurotrophic factors CDNF and MANF: structure, physiological functions and therapeutic potential. *Neurobiology of Disease,* 97, 90-102.

Lindahl M, Danilova T, Palm E, Pulkkila P, Voikar V, Hakonen E, Ustinov J, Andressoo J-O, Harvery B, Otonkoski T, Rossi J and Saarma M. 2014. MANF is indispensable for the proliferation and survival of pancreatic β-cells. *Cell Reports,* 7 (2): 366-75.

Lindholm, D., E. A. Mercer, L. Y. Yu, Y. Chen, J. Kukkonen, L. Korhonen, and U. Arumae. 2002. Neuronal apoptosis inhibitory protein: Structural requirements for hippocalcin binding and effects on survival of NGF-dependent sympathetic neurons. *Biochim. Biophys. Acta.* 1600:138-147.

Lindholm, P., and M. Saarma. 2010. Novel CDNF/MANF family of neurotrophic factors. *Dev. Neurobiol.* 70:360-371.

Lindholm, P., M. H. Voutilainen, J. Lauren, J. Peranen, V. M. Leppanen, J. O. Andressoo, M. Lindahl, S. Janhunen, N. Kalkkinen, T. Timmusk, R. K. Tuominen, and M. Saarma. 2007. Novel neurotrophic factor CDNF protects and rescues midbrain dopamine neurons in vivo. *Nature.* 448:73-77.

Lindström, R., P. Lindholm, J. Kallijärvi, Y. Li-ying, T. P. Piepponen, U. Arumäe, M. Saarma and T. I. Heino, 2013. Characterization of the Structural and Functional Determinants of MANF/CDNF in Drosophila In Vivo Model. PLOS One 8 (9), e73928.

Marino, Giada, Ulrich Eckhard, and Christopher M. Overall, Protein Termini and Their Modifications Revealed by Positional Proteomics. 2015, ACS Chem. Biol. 10:1754-1764

Nadella R, Voutilainen M H, Saarma M, Gonzalez-Barrios J A, Leon-Chavez B A, Jiménez J M, Jiménez S H, Escobedo L, Martinez-Fong D. Transient transfection of human CDNF gene reduces the 6-hydroxydopamine-induced neuroinflammation in the rat substantia nigra. *J. Neuroinflammation.* 11:209, 2014.

Neves J, Zhu J, Sousa-Victor P, Konjikusic M, Riley R, Chew S, Qi Y, Jasper H, Lamba D A, Immune modulation by MANF promotes tissue repair and regenerative success in the retina. *Science* 2016 Jul. 1; 353 (6294).

Oakes and Papa, Annu. Rev. Pathol. Mech. Dis. 2015. 10:173-94.

Parkash, V., P. Lindholm, J. Peranen, N. Kalkkinen, E. Oksanen, M. Saarma, V. M. Leppanen, and A. Goldman. 2009. The structure of the conserved neurotrophic factors MANF and CDNF explains why they are bifunctional. *Protein Eng. Des. Sel.* 22:233-241.

Penttinen A M, I. Suleymanova, K Albert, J Anttila, M H Voutilainen, M Airavaara. 2016 Characterization of a new low-dose 6-hydroxydopamine model of Parkinson's disease in rat. *J Neurosci Res*. January 13. doi: 10.1002/jnr.23708

Shibata, N. 2001. Transgenic mouse model for familial amyotrophic lateral sclerosis with superoxide dismutase-1 mutation. *Neuropathology* 21 (1): 82-92

Sun, Y. F., L. Y. Yu, M. Saarma, and U. Arumae. 2003. Mutational analysis of N-Bak reveals different structural requirements for antiapoptotic activity in neurons and proapoptotic activity in nonneuronal cells. *Mol. Cell. Neurosci.* 23:134-143.

Sun, Y. F., L. Y. Yu, M. Saarma, T. Timmusk, and U. Arumae. 2001. Neuron-specific Bcl-2 homology 3 domain-only splice variant of Bak is anti-apoptotic in neurons, but pro-apoptotic in non-neuronal cells. *J. Biol. Chem.* 276:16240-16247.

Voutilainen, M. H., S. Back, J. Peranen, P. Lindholm, A. Raasmaja, P. T. Mannisto, M. Saarma, and R. K. Tuominen. 2011. Chronic infusion of CDNF prevents 6-OHDA-induced deficits in a rat model of Parkinson's disease. *Exp. Neurol.* 228:99-108.

Voutilainen, M. H., S. Back, E. Porsti, L. Toppinen, L. Lindgren, P. Lindholm, J. Peranen, M. Saarma, and R. K. Tuominen. 2009. Mesencephalic astrocyte-derived neurotrophic factor is neurorestorative in rat model of Parkinson's disease. *J. Neurosci.* 29:9651-9659. doi: 10.1523/JNEUROSCI.0833-09.2009.

Voutilainen, M H, Arumãe U, Airavaara M, Saarma M. 2015 Therapeutic potential of the endoplasmic reticulum located and secreted CDNF/MANF family of neurotrophic factors in Parkinson's disease. *FEBS letters* 589 3739-3748.

Voutilainen M H, De Lorenzo F, Stepanova P, Bäck S, Yu L Y, Lindholm P, Pörsti E, Saarma M, Männistö P T, Tuominen R K 2017 Evidence for an Additive Neurorestorative Effect of Simultaneously Administered CDNF and GDNF in Hemiparkinsonian Rats: Implications for Different Mechanism of Action. eNeuro. March 13; 4 (1)

Yu, L. Y., and U. Arumae. 2008. Survival assay of transiently transfected dopaminergic neurons. *J. Neurosci. Methods.* 169:8-15.

Yu, L. Y., E. Jokitalo, Y. F. Sun, P. Mehlen, D. Lindholm, M. Saarma, and U. Arumae. 2003. GDNF-deprived sympathetic neurons die via a novel nonmitochondrial pathway. *J. Cell Biol.* 163:987-997.

Yu, L. Y., M. Saarma, and U. Arumae. 2008. Death receptors and caspases but not mitochondria are activated in the GDNF- or BDNF-deprived dopaminergic neurons. *J. Neurosci.* 28:7467-7475.

Zhao H, Liu Y, Cheng L, Liu B, Zhang W, Guo Y J, Nie L. 2013 Mesencephalic astrocyte-derived neurotrophic factor inhibits oxygen-glucose deprivation-induced cell damage and inflammation by suppressing endoplasmic reticulum stress in rat primary astrocytes. *J. Mol. Neurosci.* 51 (3): 671-8, 2013.

CITED PATENT PUBLICATIONS

EP58481
EP1969003
U.S. Pat. No. 3,773,919
WO2007068803
WO2009133247
WO2013034805
WO2014191630
WO2016057579

The invention claimed is:

1. A therapeutically active C-terminal cerebral dopamine neurotrophic factor (CDNF) fragment consisting of SEQ ID NO:4, or a sequence which has at least 98% homology or sequence identity with the sequence of SEQ ID NO: 4, wherein said C-terminal CDNF fragment is a cell membrane penetrating peptide and has a protective effect on neuronal cells.

2. The C-terminal CDNF fragment according to claim 1, wherein the sequence which has at least 98% homology or sequence identity with the sequence of SEQ ID NO:4 comprises sequence CKGC at positions 32-35 of SEQ ID NO:4, wherein the sequence CKGC corresponds to SEQ ID NO:12.

3. The C-terminal CDNF fragment according to claim 1, wherein said C-terminal CDNF fragment comprises the C-terminal amino acid L in position 61 of SEQ ID NO:4.

4. The C-terminal CDNF fragment according to claim 1, wherein the fragment further comprises modifications protecting the fragment from enzymatic degradation selected from the group consisting of amidation of the C-terminus and acetylation of the N-terminus.

5. A pharmaceutical composition comprising the C-terminal CDNF fragment of claim 1 and a member selected from the group consisting of a physiologically acceptable carrier, a buffer, an excipient, a preservative, a stabilizer, and combinations thereof.

6. A therapeutically active C-terminal cerebral dopamine neurotrophic factor (CDNF) fragment consisting of SEQ ID NO:4, wherein said C-terminal CDNF fragment is a cell membrane penetrating peptide and has a protective effect on neuronal cells.

7. A method of treating a degenerative disease, type 1 or type 2 diabetes, or a retinal disease comprising administering to a patient in need thereof an effective amount of the C-terminal CDNF fragment of claim 1.

8. The method according to claim 7, wherein the method treats a degenerative disease in the patient, wherein the degenerative disease comprises a neurodegenerative disease.

9. The method according to claim 8, wherein said neurodegenerative disease comprises a central nervous system (CNS) disease selected from the group consisting of: Alzheimer's disease, Parkinson's disease, multiple system atrophy, amyotrophic lateral sclerosis, frontotemporal lobar degeneration, dementia with Lewy bodies, mild cognitive impairment, Huntington's disease, traumatic brain injury, drug addiction, and stroke.

10. The method according to claim 7, wherein the method treats type 1 or type 2 diabetes in the patient.

11. The method according to claim 7, wherein the method treats a retinal disorder in the patient.

12. The method according to claim 7, wherein said C-terminal CDNF fragment is administered by intravenous, intraperitoneal, peripheral, subcutaneous, intrathecal, intracerebroventricular, intranasal, transdermal, intracerebral, intramuscular, intraocular, or intraarterial administration, or said fragment is administered via a viral expression vector.

13. The method according to claim 7, wherein the C-terminal CDNF fragment comprises modifications protecting the fragment from enzymatic degradation selected from the group consisting of amidation of the C-terminus and acetylation of the N-terminus.

* * * * *

SEQUENCE LISTING

<160> NUMBER OF SEQ ID NOS: 14

<210> SEQ ID NO 1
<211> LENGTH: 81
<212> TYPE: PRT
<213> ORGANISM: Homo sapiens

<400> SEQUENCE: 1

Met Pro Ala Met Lys Ile Cys Glu Lys Leu Lys Lys Leu Asp Ser Gln
1 5 10 15

Ile Cys Glu Leu Lys Tyr Glu Lys Thr Leu Asp Leu Ala Ser Val Asp
20 25 30

Leu Arg Lys Met Arg Val Ala Glu Leu Lys Gln Ile Leu His Ser Trp
35 40 45

Gly Glu Glu Cys Arg Ala Cys Ala Glu Lys Thr Asp Tyr Val Asn Leu
50 55 60

Ile Gln Glu Leu Ala Pro Lys Tyr Ala Ala Thr His Pro Lys Thr Glu
65 70 75 80

Leu

<210> SEQ ID NO 2
<211> LENGTH: 78
<212> TYPE: PRT
<213> ORGANISM: Homo sapiens

<400> SEQUENCE: 2

Ile Cys Glu Lys Leu Lys Lys Lys Asp Ser Gln Ile Cys Glu Leu Lys
1 5 10 15

Tyr Asp Lys Gln Ile Asp Leu Ser Thr Val Asp Leu Lys Lys Leu Arg
20 25 30

Val Lys Glu Leu Lys Lys Ile Leu Asp Asp Trp Gly Glu Thr Cys Lys
35 40 45

Gly Cys Ala Glu Lys Ser Asp Tyr Ile Arg Lys Ile Asn Glu Leu Met
50 55 60

Pro Lys Tyr Ala Pro Lys Ala Ala Ser Ala Arg Thr Asp Leu
65 70 75

<210> SEQ ID NO 3
<211> LENGTH: 81
<212> TYPE: PRT
<213> ORGANISM: Homo sapiens
<220> FEATURE:
<221> NAME/KEY: VARIANT
<222> LOCATION: 53..54
<223> OTHER INFORMATION: Xaa is any amino acid

<400> SEQUENCE: 3

Met Pro Ala Met Lys Ile Cys Glu Lys Leu Lys Lys Leu Asp Ser Gln
1 5 10 15

Ile Cys Glu Leu Lys Tyr Glu Lys Thr Leu Asp Leu Ala Ser Val Asp
20 25 30

Leu Arg Lys Met Arg Val Ala Glu Leu Lys Gln Ile Leu His Ser Trp
35 40 45

Gly Glu Glu Cys Xaa Xaa Cys Ala Glu Lys Thr Asp Tyr Val Asn Leu
50 55 60

Ile Gln Glu Leu Ala Pro Lys Tyr Ala Ala Thr His Pro Lys Thr Glu
65 70 75 80

Leu

<210> SEQ ID NO 4
<211> LENGTH: 61
<212> TYPE: PRT
<213> ORGANISM: Homo sapiens

<400> SEQUENCE: 4

```
Lys Tyr Glu Lys Thr Leu Asp Leu Ala Ser Val Asp Leu Arg Lys Met
1               5                   10                  15

Arg Val Ala Glu Leu Lys Gln Ile Leu His Ser Trp Gly Glu Glu Cys
            20                  25                  30

Arg Ala Cys Ala Glu Lys Thr Asp Tyr Val Asn Leu Ile Gln Glu Leu
        35                  40                  45

Ala Pro Lys Tyr Ala Ala Thr His Pro Lys Thr Glu Leu
    50                  55                  60
```

<210> SEQ ID NO 5
<211> LENGTH: 63
<212> TYPE: PRT
<213> ORGANISM: Homo sapiens

<400> SEQUENCE: 5

```
Lys Tyr Asp Lys Gln Ile Asp Leu Ser Thr Val Asp Leu Lys Lys Leu
1               5                   10                  15

Arg Val Lys Glu Leu Lys Lys Ile Leu Asp Asp Trp Gly Glu Thr Cys
            20                  25                  30

Lys Gly Cys Ala Glu Lys Ser Asp Tyr Ile Arg Lys Ile Asn Glu Leu
        35                  40                  45

Met Pro Lys Tyr Ala Pro Lys Ala Ala Ser Ala Arg Thr Asp Leu
    50                  55                  60
```

<210> SEQ ID NO 6
<211> LENGTH: 68
<212> TYPE: PRT
<213> ORGANISM: Homo sapiens
<220> FEATURE:
<221> NAME/KEY: VARIANT
<222> LOCATION: 38..39
<223> OTHER INFORMATION: Xaa is any amino acid.

<400> SEQUENCE: 6

```
Gln Ile Cys Glu Leu Lys Tyr Asp Lys Gln Ile Asp Leu Ser Thr Val
1               5                   10                  15

Asp Leu Lys Lys Leu Arg Val Lys Glu Leu Lys Lys Ile Leu Asp Asp
            20                  25                  30

Trp Gly Glu Thr Cys Xaa Xaa Cys Ala Glu Lys Ser Asp Tyr Ile Arg
        35                  40                  45

Lys Ile Asn Glu Leu Met Pro Lys Tyr Ala Pro Lys Ala Ala Ser Ala
    50                  55                  60

Arg Thr Asp Leu
65
```

<210> SEQ ID NO 7
<211> LENGTH: 161
<212> TYPE: PRT
<213> ORGANISM: Homo sapiens

<400> SEQUENCE: 7

```
Gln Glu Ala Gly Gly Arg Pro Gly Ala Asp Cys Glu Val Cys Lys Glu
1               5                   10                  15

Phe Leu Asn Arg Phe Tyr Lys Ser Leu Ile Asp Arg Gly Val Asn Phe
```

```
            20                  25                  30

Ser Leu Asp Thr Ile Glu Lys Glu Leu Ile Ser Phe Cys Leu Asp Thr
        35                  40                  45

Lys Gly Lys Glu Asn Arg Leu Cys Tyr Tyr Leu Gly Ala Thr Lys Asp
    50                  55                  60

Ala Ala Thr Lys Ile Leu Ser Glu Val Thr Arg Pro Met Ser Val His
65                  70                  75                  80

Met Pro Ala Met Lys Ile Cys Glu Lys Leu Lys Lys Leu Asp Ser Gln
                85                  90                  95

Ile Cys Glu Leu Lys Tyr Glu Lys Thr Leu Asp Leu Ala Ser Val Asp
            100                 105                 110

Leu Arg Lys Met Arg Val Ala Glu Leu Lys Gln Ile Leu His Ser Trp
        115                 120                 125

Gly Glu Glu Cys Arg Ala Cys Ala Glu Lys Thr Asp Tyr Val Asn Leu
    130                 135                 140

Ile Gln Glu Leu Ala Pro Lys Tyr Ala Ala Thr His Pro Lys Thr Glu
145                 150                 155                 160

Leu


<210> SEQ ID NO 8
<211> LENGTH: 100
<212> TYPE: PRT
<213> ORGANISM: Homo sapiens

<400> SEQUENCE: 8

Gln Glu Ala Gly Gly Arg Pro Gly Ala Asp Cys Glu Val Cys Lys Glu
1               5                   10                  15

Phe Leu Asn Arg Phe Tyr Lys Ser Leu Ile Asp Arg Gly Val Asn Phe
            20                  25                  30

Ser Leu Asp Thr Ile Glu Lys Glu Leu Ile Ser Phe Cys Leu Asp Thr
        35                  40                  45

Lys Gly Lys Glu Asn Arg Leu Cys Tyr Tyr Leu Gly Ala Thr Lys Asp
    50                  55                  60

Ala Ala Thr Lys Ile Leu Ser Glu Val Thr Arg Pro Met Ser Val His
65                  70                  75                  80

Met Pro Ala Met Lys Ile Cys Glu Lys Leu Lys Lys Leu Asp Ser Gln
                85                  90                  95

Ile Cys Glu Leu
            100


<210> SEQ ID NO 9
<211> LENGTH: 158
<212> TYPE: PRT
<213> ORGANISM: Homo sapiens

<400> SEQUENCE: 9

Leu Arg Pro Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Thr Ile
            20                  25                  30

Glu Asn Glu Leu Ile Lys Phe Cys Arg Glu Ala Arg Gly Lys Glu Asn
        35                  40                  45

Arg Leu Cys Tyr Tyr Ile Gly Ala Thr Asp Asp Ala Ala Thr Lys Ile
    50                  55                  60

Ile Asn Glu Val Ser Lys Pro Leu Ala His His Ile Pro Val Glu Lys
65                  70                  75                  80
```

-continued

```
Ile Cys Glu Lys Leu Lys Lys Lys Asp Ser Gln Ile Cys Glu Leu Lys
                85                  90                  95

Tyr Asp Lys Gln Ile Asp Leu Ser Thr Val Asp Leu Lys Lys Leu Arg
            100                 105                 110

Val Lys Glu Leu Lys Lys Ile Leu Asp Asp Trp Gly Glu Thr Cys Lys
        115                 120                 125

Gly Cys Ala Glu Lys Ser Asp Tyr Ile Arg Lys Ile Asn Glu Leu Met
    130                 135                 140

Pro Lys Tyr Ala Pro Lys Ala Ala Ser Ala Arg Thr Asp Leu
145                 150                 155


<210> SEQ ID NO 10
<211> LENGTH: 95
<212> TYPE: PRT
<213> ORGANISM: Homo sapiens

<400> SEQUENCE: 10

Leu Arg Pro Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Thr Ile
            20                  25                  30

Glu Asn Glu Leu Ile Lys Phe Cys Arg Glu Ala Arg Gly Lys Glu Asn
        35                  40                  45

Arg Leu Cys Tyr Tyr Ile Gly Ala Thr Asp Asp Ala Ala Thr Lys Ile
    50                  55                  60

Ile Asn Glu Val Ser Lys Pro Leu Ala His His Ile Pro Val Glu Lys
65                  70                  75                  80

Ile Cys Glu Lys Leu Lys Lys Lys Asp Ser Gln Ile Cys Glu Leu
                85                  90                  95


<210> SEQ ID NO 11
<211> LENGTH: 4
<212> TYPE: PRT
<213> ORGANISM: Homo sapiens

<400> SEQUENCE: 11

Cys Arg Ala Cys
1


<210> SEQ ID NO 12
<211> LENGTH: 4
<212> TYPE: PRT
<213> ORGANISM: Homo sapiens

<400> SEQUENCE: 12

Cys Lys Gly Cys
1


<210> SEQ ID NO 13
<211> LENGTH: 4
<212> TYPE: PRT
<213> ORGANISM: Homo sapiens

<400> SEQUENCE: 13

Lys Thr Glu Leu
1


<210> SEQ ID NO 14
<211> LENGTH: 4
<212> TYPE: PRT
```

-continued

```
<213> ORGANISM: Homo sapiens

<400> SEQUENCE: 14

Arg Thr Asp Leu
1
```